(12) United States Patent
Hedman

(10) Patent No.: US 7,837,932 B2
(45) Date of Patent: Nov. 23, 2010

(54) METHOD FOR REMOVING OR TREATING HARMFUL BIOLOGICAL ORGANISMS AND CHEMICAL SUBSTANCES

(75) Inventor: David E. Hedman, Ojai, CA (US)

(73) Assignee: Thermapure, Inc., Ventura, CA (US)

(*) Notice: Subject to any disclaimer, the term of this patent is extended or adjusted under 35 U.S.C. 154(b) by 732 days.

(21) Appl. No.: 11/773,616

(22) Filed: Jul. 5, 2007

(65) Prior Publication Data

US 2008/0014111 A1 Jan. 17, 2008

Related U.S. Application Data

(63) Continuation-in-part of application No. 10/014,727, filed on Dec. 10, 2001, which is a continuation of application No. 09/321,915, filed on May 28, 1999, now Pat. No. 6,327,812, application No. 11/773,616, filed on Jul. 5, 2007, which is a continuation-in-part of application No. 10/644,553, filed on Aug. 19, 2003, which is a continuation-in-part of application No. 10/371,826, filed on Feb. 20, 2003, which is a continuation-in-part of application No. 10/313,901, filed on Dec. 5, 2002, now abandoned, application No. 11/773,616, which is a continuation-in-part of application No. 11/428,767, filed on Jul. 5, 2006, now abandoned, which is a continuation-in-part of application No. 10/313,901, filed on Dec. 5, 2002, now abandoned, application No. 11/773,616, which is a continuation-in-part of application No. 11/122,579, filed on May 4, 2005, which is a continuation-in-part of application No. 10/917,792, filed on Aug. 12, 2004, now abandoned, which is a continuation-in-part of application No. 10/644,553, filed on Aug. 19, 2003, which is a continuation-in-part of application No. 10/371,826, filed on Feb. 20, 2003, which is a continuation-in-part of application No. 10/313,901, filed on Dec. 5, 2002, now abandoned, which is a continuation-in-part of application No. 10/218,150, filed on Aug. 12, 2002, now Pat. No. 6,892,491, which is a continuation-in-part of application No. 09/768,680, filed on Jan. 24, 2001, now abandoned, which is a continuation-in-part of application No. 09/321,915, filed on May 28, 1999, now Pat. No. 6,327,812, application No. 11/773,616, which is a continuation-in-part of application No. 10/917,792, filed on Aug. 12, 2004, now abandoned, which is a continuation-in-part of application No. 10/371,826, filed on Feb. 20, 2003, which is a continuation-in-part of application No. 10/313,901, filed on Dec. 5, 2002, now abandoned, application No. 11/773,616, which is a continuation-in-part of application No. 10/371,826, filed on Feb. 20, 2003, which is a continuation-in-part of application No. 10/313,901, filed on Dec. 5, 2002, now abandoned.

(60) Provisional application No. 60/806,646, filed on Jul. 6, 2006, provisional application No. 60/358,222, filed on Feb. 20, 2002, provisional application No. 60/358,223, filed on Feb. 20, 2002, provisional application No. 60/339,184, filed on Dec. 7, 2001.

(51) Int. Cl.
*A61L 2/08* (2006.01)
*A01M 19/00* (2006.01)

(52) U.S. Cl. .................................. 422/22; 43/132.1

(58) Field of Classification Search .................. None
See application file for complete search history.

(56) References Cited

U.S. PATENT DOCUMENTS

| | | | |
|---|---|---|---|
| 923,368 A | 6/1909 | Myser | |
| 1,885,854 A | 11/1932 | Montellano | |
| 3,107,974 A * | 10/1963 | Potapenko | 422/4 |
| 3,750,327 A | 8/1973 | Thybault | |
| 3,846,072 A | 11/1974 | Patterson | |
| 3,966,407 A * | 6/1976 | Zuckerberg et al. | 422/4 |
| 4,676,152 A * | 6/1987 | Tsuji et al. | 99/468 |
| 4,817,329 A | 4/1989 | Forbes | |
| 4,864,942 A | 9/1989 | Fochtman et al. | |
| 4,953,320 A | 9/1990 | Nelson | |
| 4,958,456 A | 9/1990 | Chaudoin et al. | |
| 4,961,283 A | 10/1990 | Forbes | |
| 4,989,363 A | 2/1991 | Doernemann | |
| 5,022,165 A | 6/1991 | Beswick | |
| 5,058,313 A | 10/1991 | Tallon | |
| 5,219,226 A | 6/1993 | James | |
| 5,293,700 A * | 3/1994 | Ishii | 34/225 |
| 5,349,778 A | 9/1994 | Chu | |
| 5,387,403 A | 2/1995 | Ikeuchi et al. | |
| 5,442,876 A | 8/1995 | Pedersen | |
| 5,491,092 A | 2/1996 | Colvin | |
| 5,768,907 A | 6/1998 | Lee | |
| 5,806,238 A | 9/1998 | Brenner | |
| 5,874,050 A * | 2/1999 | Matias | 422/120 |
| 5,960,558 A * | 10/1999 | Bourgault | 34/495 |
| 5,979,472 A | 11/1999 | Lowery et al. | |
| 6,141,901 A | 11/2000 | Johnson et al. | |
| 6,162,393 A | 12/2000 | De Bruiju et al. | |
| 6,199,770 B1 | 3/2001 | King et al. | |
| 6,327,812 B1 | 12/2001 | Hedman et al. | |
| 6,451,152 B1 | 9/2002 | Holmes et al. | |
| 6,612,067 B2 | 9/2003 | Topp | |

(Continued)

Primary Examiner—Elizabeth L McKane
(74) Attorney, Agent, or Firm—Kelly Lowry & Kelley, LLP

(57) ABSTRACT

The present invention relates to methods of sanitizing structures, buildings, passenger occupiable vehicles, and other enclosed or enclosable spaces. More particularly, the present invention relates to a method for killing and/or removing pests and their allergens, bacteria, viruses, fungi, molds, volatile organic compounds and other dangerous substances, from such enclosures.

41 Claims, 21 Drawing Sheets

U.S. PATENT DOCUMENTS

| | | | |
|---|---|---|---|
| 6,656,424 B1 * | 12/2003 | Deal | 422/3 |
| 6,892,491 B2 | 5/2005 | Hedman | |
| 6,962,619 B1 * | 11/2005 | DeRosa et al. | 95/267 |
| 2001/0025570 A1 | 10/2001 | Fukushima | |
| 2002/0189154 A1 | 12/2002 | Hedman | |
| 2003/0100465 A1 | 5/2003 | Kilkenny et al. | |
| 2003/0230477 A1 | 12/2003 | Fink et al. | |
| 2004/0028554 A1 | 2/2004 | Hedman | |

* cited by examiner

METHOD FOR REMOVING OR TREATING HARMFUL BIOLOGICAL ORGANISMS AND CHEMICAL SUBSTANCES

BACKGROUND OF THE INVENTION

The present invention relates to methods of sanitizing structures, buildings, passenger occupiable vehicles, and other enclosed or enclosable spaces. More particularly, the present invention relates to a method for killing and/or removing pests and their allergens, bacteria, viruses, fungi, molds, volatile organic compounds and other dangerous substances.

It is a common problem that pests, such as insects, rodents and birds, find their way into homes, hotels and other structures. For example, mice, rats, other rodents and birds often find access into a home or building through open doors, crevices, etc., and nest and breed within the house, particularly within the winter months.

The presence of such rodents, or nesting birds or bats, can also introduce other pests and microbes into the structure. For example, fleas, lice and beg bugs often find there way into homes, hotels, etc., by transmission of birds and rodents which nest within the eaves or within the structure of the home or hotel. There are at least 70 different kinds of bed bugs across the world. The blood-sucking parasites are wingless, dark reddish-brown, oval and flat insects. Full-size adults are typically less than one quarter inch long, and mature in about four weeks after hatching, if a host is available. Bed bugs can endure freezing temperatures and use a variety of hosts besides humans, including poultry, rodents, dogs, cats, birds and bats. Although humans rarely feel the approximately 15 minute long bite, some people show sensitive reactions to it. An indication of bed bugs is small blood spots on bed sheets. Bed bugs hide in cracks and crevices during the day, and come out at night to feed. They are found around mattresses, behind picture frames, in night stands, stuffed furniture, behind loose wallpaper, and other enclosed spaces. They will crawl a substantial distance to obtain a blood meal. This is particularly a problem in the hotel industry, where customers can pay several hundred dollars a night for their room, and awake in the room with bed bug bites and bloodied sheets.

In desert settings, it is not uncommon for scorpions to infest homes, and occasionally sting unsuspecting adults or curious children or animals. The scorpions gain access to the dwelling through holes or crevices in the house and are attracted to the moisture and cooler temperatures.

A large number of methods have been developed for killing insects, such as termites, in buildings. The most widely used method is tenting the building, then filling the building with a toxic gas for a period of time sufficient to kill termites or other selected insects. This method is effective for killing termites and other insects. However, this method generally requires 12 to 72 hours to be effective, requiring building occupants to move out and businesses to be closed for approximately a three day period to insure proper venting of toxic material and/or gas. Tenting the building with heavy tarpaulins requires workers to walk and arrange the tarpaulins on the roof, often damaging the roof system. Food and medications must be placed in sealed containers or removed. Generally the entire building must be treated, even if the infestation is localized.

Techniques of varying effectiveness have been developed using heated air or very cold air to kill termites and other organisms. Typical of these are the methods disclosed by Charles Forbes in U.S. Pat. No. 4,817,329, in which wood destroying insects, e.g., termites, are killed by applying a heated gas, such as heated air, to wooden surfaces or the like until the core of wooden structures is heated to a temperature typically about 120° F. to 135° F. This method has been found to be very effective for killing termites. Another alternative to the toxic gas method is disclosed by James J. Chaudoin, et al. in U.S. Pat. No. 4,958,456, in which insects, e.g., roaches, fleas and beetles, are killed by a treatment of building spaces with boric acid and heat. However, the methods disclosed in the Forbes patent are quite complex in the preparation of the building. An enclosing tent structure must be formed around the building to be decontaminated, as the termites and wood eating insects are typically found in the framing, shingles, and outer panels of the building. Tenting the building with heavy tarpaulins requires workers to walk and arrange the tarpaulins on the roof, often damaging the roof system.

Other organisms, such as bacteria, viruses, fungi, and molds such as, but not limited to, *aspergillus oryzae, aspergillus terreus, aspergillus versicolor, cladosporium hergbarum, stachybotrys chartarum, penicillium aurantiogriseum, pencillium chrsogenum, pencillium gladrum* and *fusarium oxysporum*, are a serious health hazard even when dead. Many people are allergic to the dust-like remains and residue, i.e., allergens, of these organisms that can also cause serious health problems. This is a particular problem to persons suffering from asthma, bronchitis, pneumoconious and other respiratory ailments, and is a common contributing factor to sick building syndrome (SBS).

It is also well-known that the heated air causes certain molds, fungi, etc. to sporulate, thus releasing spores into the structure and thus dispersing the harmful biological agents and possibly contaminating the structure to a greater degree than originally presented. The use of positive pressure within the structure, as described in Forbes and Hedman et al., further increase the likelihood that the biological contaminants will be dispersed throughout the structure. Forbes also discloses that the heated air can be vented from open windows and the like. However, when treating a contaminated building having harmful viruses, toxic molds, etc., it is not desirable to release such contagions into the air.

Volatile organic compounds (VOCs) have also been implicated as a possible cause of SBS. VOCs can originate from a variety of sources. Commercial examples include by-products of printing shop operations, office machine repairs, blueprint production, photographic processing and food service operations. In residences, such VOCs can include hobbyist products, cosmetics, perfumes, personal hygiene products, aerosol sprays, tobacco smoke, pet urine and even small emissions from the bodies of the occupants. Off-gassing of VOCs is often a common by-product of various building/construction materials, for example paints, adhesives, plastics, carpeting, etc.

Such VOCs are implicated with SBS for mostly two reasons. First, the health effects from exposure to VOCs are consistent with SBS, ranging from irritant effects such as unpleasant odors and mucous membrane irritation, through general systemic effects such as fatigue, nausea, and difficulty concentrating. In addition, they may be of importance because some of them have been shown to have carcinogenic or adverse reproductive effects. Second, indoor concentrations of VOCs, particularly in new buildings, are often greatly elevated with respect to outdoor VOC concentrations. In fact, indoor VOC concentrations have typically been found to be two to ten times higher than outdoor concentrations, and indoor concentrations as much as 100 times higher than outdoor concentrations have been reported in new buildings.

In the northeastern parts of the United States, it is common for heating oil to be delivered and used in the heating of the home during the winter months. The oil can spill, and the fuel oil fumes and odors can infiltrate the house over time and contribute to SBS.

Passenger occupiable vehicles, such as trains, buses, airplanes, etc. also include building/construction materials which are known to off-gas VOC's. Also, the fuel, oil, and grease fumes and odors can infiltrate the passenger compartments of such vehicles and build-up within the seats, carpets, etc. over time. Due to the great number of people regularly traveling in such vehicles, there is an increased chance of coming into contact with contagious bacterium or viruses that can cause illness. Other organisms, such as fungi, and toxic molds can also be potentially found in such vehicles. As the company owning such vehicles necessarily must keep the vehicles running nearly constantly in order to realize the expected profit, such vehicles are rarely cleaned thoroughly. Even if the surfaces are superficially vacuumed and wiped down, there still remain live and dead organisms such as lice, mites, fungi, toxic molds, bacterium, viruses, VOCs, oxidized odors, and potentially insects which may have infested the vehicle, particularly those where food is prepared or served.

A common problem in the wine industry is cork taint. This is most accurately described as a "moldy" or "musty" smell that masks or dominates the fruit aroma of wine and reduces the overall wine quality. Infected wines are said to be "corked" or "corky". The causes of cork taint are believed to be two-fold. Molds may be originally present in raw cork bark or in wood used for barrels or other winery equipment or facilities, and can infect cork or wood in storage. Ironically, chemicals which react with the molds are introduced by methods and equipment used for keeping the production environment sterile and safe. One culprit is chlorine bleach used in cork processing and also as a routine disinfectant in wineries. Another is atmospheric off-gassing from plastic equipment. TCA, a common abbreviation for various chloroanisole compounds (such as 2,4,6-trichloroanisole, and 2,3,4,6-tetrachloroanisole), is also thought to be a primary cause of cork taint. Damage to the wine industry annually is estimated to be $10 Billion worldwide. A method is needed to prevent or purge TCA, and other atmospheric pollution and residue bleach, from corks and wooden barrels and structures in the production facilities. Similar problems arising from TCA are known to exist in the food and shipping industries.

When constructing new buildings, such as homes and the like, framed with wooden beams, a growing concern is the moisture content of the wood which can result in toxic-mold. Another problem is that framing lumber that has too high a moisture content may lead to shrinkage, resulting in drywall cracking and other problems in the structure. Such moisture-laden or "green" lumber typically has a moisture content between 19%-28%. In the past, construction of a home or building took six months or more, often allowing the wood to naturally dry out over time and reach a stabilized moisture content corresponding with the geographic region, typically less than 15%. It is known that for every 4% of moisture removed from the wood, a corresponding 1% of shrinkage of the wood occurs. Today, buildings and homes are often constructed in three to four months. This is insufficient time to achieve the dimensional stability and drying of the frames. Kiln dried wood, which is wood that has been previously dried in a kiln for 24-48 hours at temperatures between 170°-240° before being used in construction, is commonly being used to meet the fast construction deadlines. However, the cost of kiln-dried lumber ranges from $0.24-$0.30 per board foot, adding an additional $4,000-$5,000 additional lumber cost for a typical 2,000 square foot structure.

Accordingly, there is a need for a system and method for killing and removing biological organisms and reducing odors and volatile organic compounds in enclosures such as commercial and residential buildings, boats, vehicles and portable containers. Such a method should be non-toxic and performed in a relatively short amount of time. Such a method should also effectively kill and remove a large proportion of the dead organisms and substantially reduce volatile organic compounds. There is also a need for a method which can remove moisture from green lumber so as to speed up the construction process and eliminate mold and shrinkage concerns of framing which has too high of a moisture content. The present invention fulfills these needs and provides other related advantages.

SUMMARY OF THE INVENTION

The present invention resides in methodologies for removing and treating harmful biological organisms and chemical substances, such as from human occupiable vehicles or building structures or other enclosures. Such structures or enclosures which are contaminated with harmful microorganisms or insects, or have objects therein contaminated with such microorganisms or insects, can be treated utilizing the present invention. In accordance with the present invention, at least a portion of the structure to be treated is substantially enclosed. The structure typically comprises at least a portion of a vehicle or a building. Ambient air within the structure is heated to a predetermined temperature between 110° F. to 400° F. to cause the harmful microorganisms or insects in the structure to be destroyed or migrate into the ambient air. The temperature in the structure is monitored. The heated air from the structure is passed through a filter. In a particularly preferred embodiment, the filtered and heated air is recirculated in the portion of the structure being treated.

The ambient air within the structure can be heated using various methodologies. In one embodiment, one or more heaters are disposed within the portion of the structure to be treated. For example, the heating step may comprise the step of providing a heater within the structure that emits electromagnetic waives, such as infrared heat. The structure may also be irradiated with ultra-violet light, which serves to kill microorganisms. A hydronic heating system may be used to heat the air within the structure. Preferably, non-fossil fuels are burnt to heat the air within the structure, or electrically powered devices are used. In accordance with the present invention, a first type of heater may be used to heat the structure during an initial heating phase, while a second type of heater is used to heat the structure during a later heating phase.

Air is aggressively moved within the structure to aerosolize biological and inorganic substances to facilitate their removal. In one embodiment, a plurality of fans are positioned to create a cyclone of wind within the structure. The fans may be placed adjacent to a heater disposed within the structure.

In some cases, a contaminated portion of the structure is physically cleaned, such as prior to the heating step. Moreover, a contaminated portion within the structure may be physically cleaned after determining that adequate treatment has occurred.

The demonitoring of the temperature in the structure step may include the step of positioning a plurality of temperature probes at predetermined locations relative to the structure. Heat-sensitive articles within the structure may be protected.

In a particularly preferred embodiment, the air within the structure is dehumidified. Moreover, the moisture content of the air within the structure may be monitored.

The heated air from the structure may be passed through a filter and/or an air scrubber positioned within or outside of the structure. The level of airborne contaminants within the structure may be monitored.

A pressure may be established within the structure, which is monitored. The pressure within the structure may be measured by manometers placed within the structures.

In one embodiment, heated air is introduced into a space within a wall. This may require forming an air inlet in the wall, as well as an air outlet in the wall. Positive air pressure may be applied due to the introduction of the heated air within the wall. Also, air may be removed from the space within the wall, effectively creating a negative pressure therein. Preferably, the air from the space within the wall is passed through a filter or air scrubber.

In another embodiment, a metal-based material, such as a metal powder, is injected into an area of the structure or applied to an area of contamination. Subsequently, the area is bombarded with electromagnetic waives, such as radio waives having a frequency that heats the metal-based material.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

As shown in the accompanying drawings for purpose of illustration, the present invention is related to a system and method for treating structures, such as human occupiable buildings, vehicles and other enclosures. In accordance with the present invention, heating of the air is primarily used to treat such structures so as to remove and/or denature harmful organic substances, such as VOCs, MVOCs (microbial volatile organic compounds), microbiological agents such as bacteria and viruses, and pests such as bed bugs, scorpions, etc. and their allergens from an enclosure. For purposes of explanation, components of the invention which are identical or similar to one another may be labeled with the identical reference number.

Figure 1:
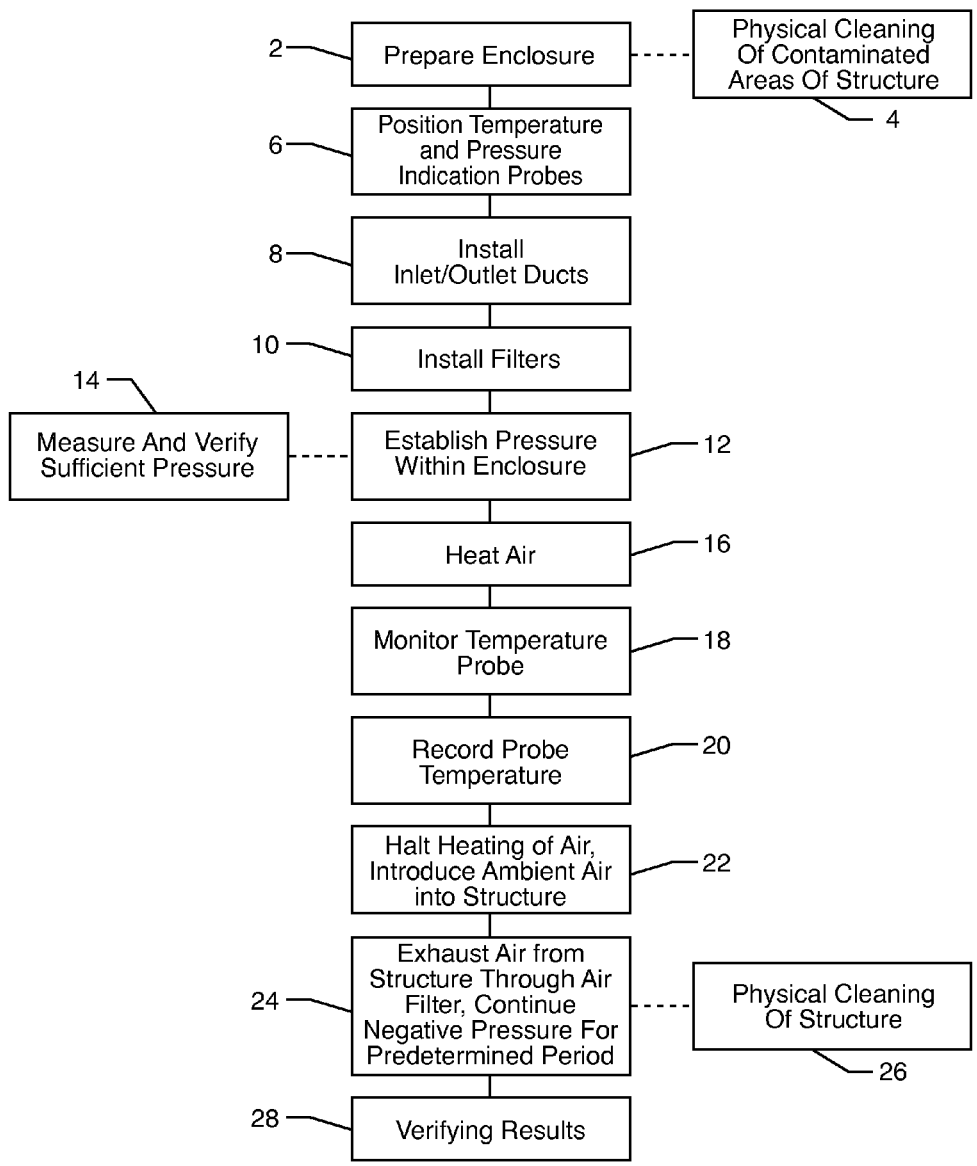
FIG. 1 is a flow-diagram illustrating the steps taken in the method of the present invention.

With reference to FIG. 1, in the operation of the system of the invention, the first step is to prepare the structure, as indicated in block (2). This may require removing all heat-sensitive items from the enclosure or, in some cases, covering heat sensitive items, such as electronic devices and plastic items, with thermal insulation material. All material that has a flash/melt point at or below the maximum temperature to be used (such as candles, lipstick, etc.) should be removed.

The preparation of the structure may also include physical cleaning of contaminated areas of the structure (4), which may be preformed while the area is under a negative pressure. This can include vacuuming, wiping, scraping, etc. of various surfaces which have been contaminated with harmful biological contaminants, such as mold, fungi or bird, rodent or insect debris, etc. In extreme cases, this may require the removal of carpeting, section of walls, etc. However, the invention is intended to neutralize and remove these biological and chemical contaminants without requiring resort to such extreme measures in most instances.

As part of preparation to building, the necessary biocides, fumigants, etc., may be selectively applied to portions of the structure to be treated. In one embodiment, particularly when treating the structure for mold and fungi, biocides and preferably boric acid, are dispersed within the structure at locations, preferably, where mold and fungi are likely to be encountered. Boric acid, $H_3BO_3$, is a white crystalline, oxygen-bearing acid of boron found in certain minerals and volcanic waters or hot springs in certain mineral deposits. Boric acid, or salts of boric acid, borates, traces of boron are necessary for growth of land plants and thus are indirectly essential for human life. In excessive quantities, however, borates may act as unselective herbicides and insecticides. The most common source of boric acid is borate, sodium tetra borate or borax, which occurs naturally in salt beds. Boric acid may be obtained by treating borate with sulfuric acid. Boric acid is commonly used as a mild antiseptic for burns and surface wounds and comprises a major ingredient in eye lotions. Importantly, boric acid is non-toxic to humans and animals and is ecologically benign in low concentrations.

Applying boric acid using conventional applicator methods and devices, i.e., dusting boric acid as a conventional insecticide as dust, spraying a solution or slurry or dispersion of boric acid, etc., coupled with heating the air within the enclosure, advantageously improves mold, fungi and pest abatement within the structure. The borates may be used in pre-treating contents of an enclosure, such as building materials, lumber, etc. or in post-treating such contents after application of heat.

A plurality of temperature and/or moisture indicating and sometimes pressure measuring probes are typically placed in predetermined locations as indicated in block (6) to assure that the required temperature levels are achieved. In some cases the probes can be read directly, although preferably they are connected by wires or wireless means to a console, so that all probes can be monitored conveniently and the data recorded in real time. It will be appreciated by those skilled in the art that a variety of probes could be used. Such probes could include remote wire probes, thermal imaging cameras to not only determine the temperature but also to ensure uniform treatment, infrared spectrometers, carbon monoxide meters, oxygen monitors, hygrometers or other moisture sensing devices, manometers or other pressure sensing devices, etc. Also, devices may be installed within the structure that measure the air flow, to ensure that adequate air flow occurs such that the entire structure is treated properly.

The enclosed structure may be substantially sealed and at least one inlet duct and at least one outlet duct installed as indicated in block (8). Generally, a plurality of inlet ducts is preferred. Although each duct may enter the enclosed structure separately, the use of one inlet duct connected to a manifold from which plural ducts extend to predetermined locations within the enclosed structure is preferred. Ducts may enter the structure through any suitable opening, such as an open window or door with the remainder of the window or door blocked by a panel. In some instances, such as when treating vehicles, tenting may actually be required or desired to treat the structure. However, in many instances such tenting is not required.

Any necessary air scrubbing filters and vacuum devices for facilitating the removal of the heated air and filtering the harmful substances therefrom, are installed, as indicated in block (10). These may be positioned within the structure, or outside of the structure or treatment area and have air from the structure directed therethrough. In addition, or alternatively, air scrubbers may be used.

When the components of the system have been properly prepared and positioned, heated air is directed into the inlet ducts (16) and the desired pressure is established within the structure (12) and the manometer or other pressure sensing device is used to verify that a sufficient pressure is present (14). In some instances, a positive pressure is actually desired wherein the ingress of heated air flow into the containment area exceeds the egress air flow from the negative air machines. Such positive pressure may be desired to force the contaminants to volatize or otherwise enter the circulated air. In other instances, a negative air pressure within the structure is desirable, by removing air more quickly than it is introduced, to ensure the removable of the contaminants therefrom and to promote circulation of the air. This is accomplished using a vacuum/blower device and filter. Using the pressure measuring manometer device, the internal pressure of the structure is measured and it is verified that sufficient negative pressure is present. Often the establishment of negative pressure is performed before any heat is introduced into the structure in order to begin the removal of any loose and aerosolized contaminants, and prevent their sporulation before heat is introduced. In some instances, neither a positive nor a negative pressure is critical. Instead, the treated air is either recirculated to the structure, or allowed to flow through an outlet duct.

Although in some of the embodiments of the present invention air is heated and pumped into the structure, such as through the inlet ducts (16), in other instances, as will be more fully described herein, the air within the structure or the portion of the structure to be treated is heated by heaters or heat exchangers placed directly within the portion of the structure to be treated. Thus, in some instances, inlets will need to be formed in the structure, tenting or the like, while yet in other instances heated air is introduced into the structure via tubing, piping or the like, and yet in other instances heating devices are present within the structure and no inlets or outlets are required.

Flow of the heated air through the enclosed structure may range in time from a few hours to several days to provide optimum results. During this time, the probes are monitored (18) and these results may be recorded in real time (20) to ensure that the intended areas within the structure are properly treated.

The heated air which has been circulated through the structure is preferably passed through an air scrubber or filter to remove the remains of the destroyed microorganisms and chemicals, such as VOCs. Biocides, such as ozone, may be added to the heated air to enhance the treatment effect. In other instances, the treatment may be to remove moisture from the structure, such as when removing moisture from the framing of a partially built structure, removing moisture from a water damaged structure which may contain mold, etc. As will be described more fully herein, when removing moisture, the heated air alone will serve to dry out and remove moisture, and dessicants and dehumidifiers and the like may also be used.

Hygrometers, or other moisture sensing devices, may be used to monitor the moisture content of the air within the structure. This can be useful, for example, when treating structures which have had water damage. Also, a very low moisture content may serve to dessicate and kill insects, mold, fungi, etc.

At any time during system operation, the inlet and outlet ducts may be moved to assure uniform temperatures throughout the structure. In some instances, it is desirable or even necessary that workers enter the structure. For example, the workers may need to monitor probes and the like, internal heaters, take temperature readings at different locations within the structure where probes are not present, use thermal imaging equipment, ascertain the progress of the treatment, etc. Given the high temperature of the air during the treatment (110° F. to 400° F.) and the potential use of fumigants and biocides, safety issues must be addressed. For example, the workers may be required to wear respirators masks so that the fumigants and biocides do not enter their eyes, nose, or mouth. The workers may need to even wear heat shielding suits in extreme situations. In other situations, tivac suits may be desirable, such as for preventing bed bugs from cleaning onto the workers' clothing. Cooling the workers may also be important, such as providing ice vests, cooling units, sources of water to hydrate the workers, etc.

After a predetermined period of time in which it has been determined that the harmful biological organisms and agents have been destroyed, the heating of air is halted and non-heated ambient air may be introduced into the structure (22). The air from the structure is often exhausted through the air filter while the negative pressure is maintained for a predetermined period of time (24). It will also be understood that the air may be passed through the air filter or air scrubber continuously during the treatment of the building. The air filter or other scrubber may be positioned within the structure itself, or be positioned outside of the structure so as to emit filtered air therefrom into the environment, or as part of a recirculation route. These steps are taken in order to prevent any viable fungi, molds, etc. from sporulating or the like as such organisms when threatened with destruction will often sporulate or form cysts or the like to facilitate the survival of the organisms and their progeny. The aggressive air flow through the structure continues to remove the harmful microorganisms, chemical substances, etc., for some time.

This entire process may often be completed in as little as one to twelve hours, for example, allowing a business to be closed for only one day or a residential structure to be fully treated during a typical work or school day. However, in certain circumstances, such as in the case of large structures or high levels of harmful substances within the structure, the process may be extended to several days or more to ensure that the structure is properly treated. It has been found that while harmful organisms are killed and removed during this process, the reduction of the VOCs actually continues for some time after treatment. Placing a filtering system within the structure and/or opening a window to allow the structure to properly vent is believed to be adequate to remove these residual compounds.

In certain instances, the structure is then physically cleaned (26) after the aforementioned steps have been performed. For example, when dealing with the Hanta virus, the health concerns of the workers dictate that the virus be killed and removed to the greatest extent possible. Then, after the virus has been destroyed and removed to the greatest extent possible utilizing the aforementioned steps, workers can enter the structure and physically remove rodent droppings and the like which may contain the neutralized viruses. Samples and specimens may be taken of the previously contaminated areas to verify the desired results (28) and a physical examination of the structure can be used to verify the removal of the contagions and harmful substances or killing of pests such as bed bugs. The sampling of the air, while heated or when cooler ambient air is introduced and removed, can also be used to verify the level of VOCs, MVOCs (microbial volatile organic compound) or pests using a high speed gas chromatograph device, sometimes referred to as an electronic nose, or the like.

Although the above description has been directed to rather large structures, such as residential or commercial buildings and passenger occupiable vehicles and the like, the present invention can also be applied to treatment of much smaller areas or objects. For example, a single room of a building may be treated by sealing the windows, doors, and other passageways of that particular room or area and treating such area, as described above. There are also instances where small personal articles, such as clothing or bedding, or even furniture is required to be treated, or a portion of the structure, but not the entire structure itself, as will be more fully discussed herein.

Figure 2:
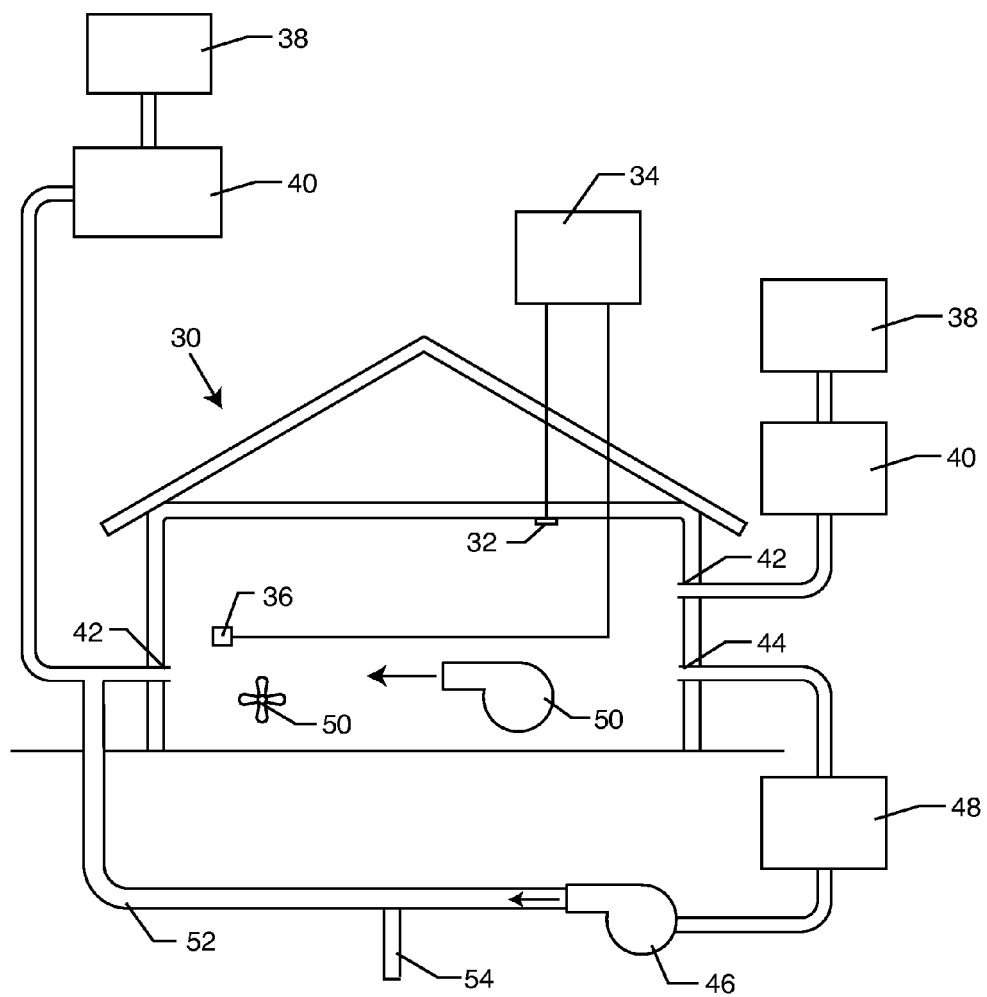
FIG. 2 is a schematic diagram showing various components of the system of the present invention installed for treatment of a building.
Figure 17:
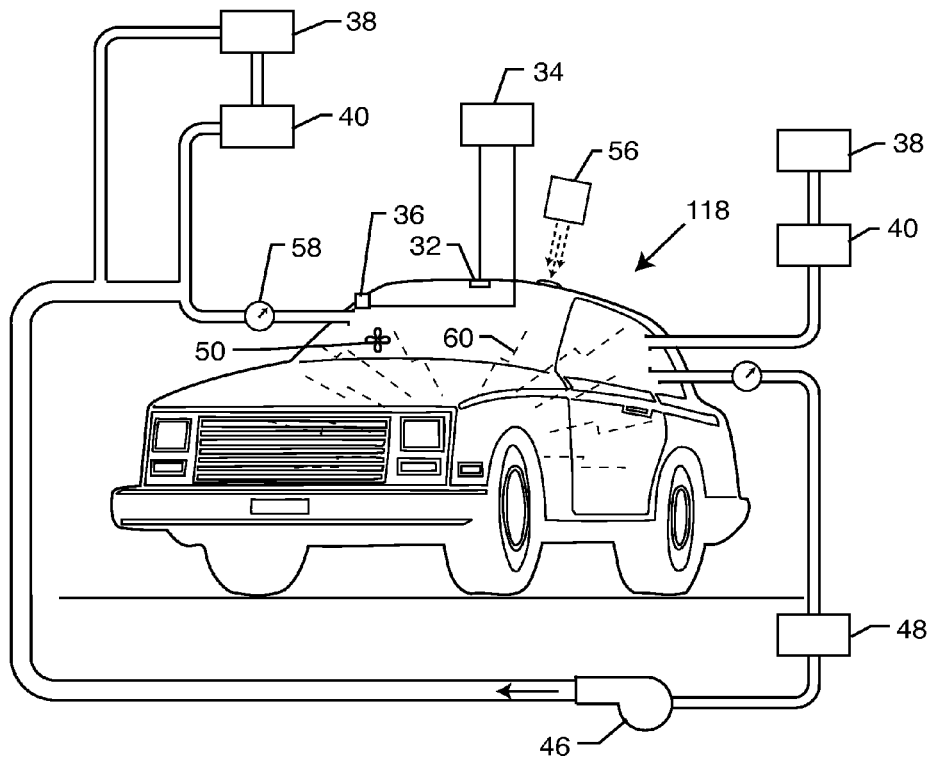
FIG. 17 is a schematic diagram showing an automobile treated in accordance with the method of the present invention.
Figure 18:
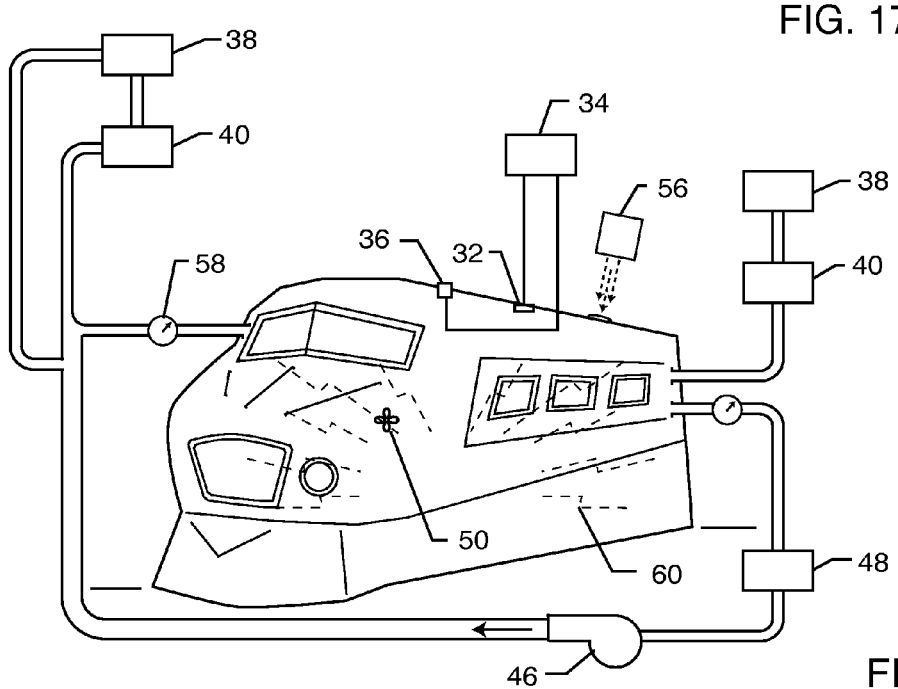
FIG. 18 is a schematic diagram showing a train treated in accordance with the present invention.
Figure 19:
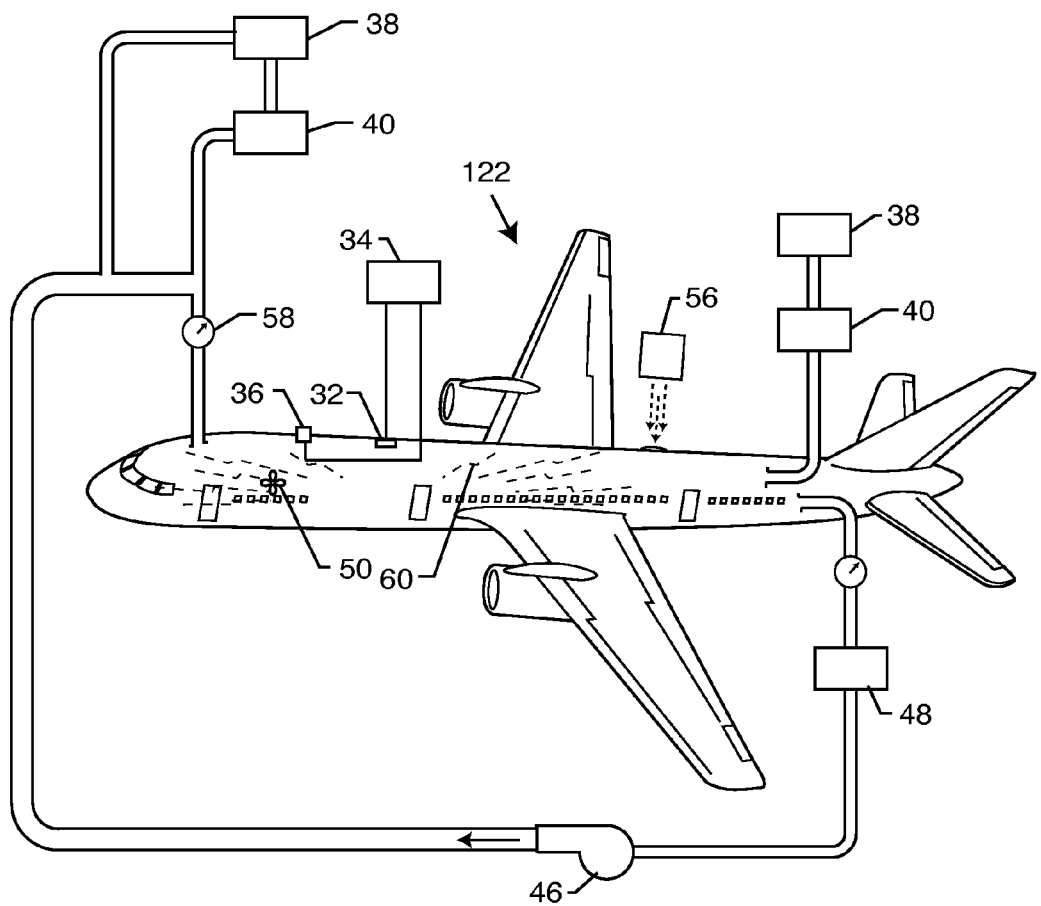
FIG. 19 is a schematic diagram illustrating an airplane treated in accordance with the present invention.

Referring now to FIG. 2, a schematic diagram shows the components of one embodiment of a system of the present invention for treating an enclosed structure 30. The enclosed structure 30 is typically a commercial or residential building, but can also be a vehicle, such as an airplane, bus, boat, automobile, etc., as illustrated in FIGS. 17-19, and as will be more fully described herein.

A plurality of temperature sensors 32 are preferably positioned at predetermined locations relative to the structure to monitor the temperature of the structure 30. These sensors 32 may have thin, elongated tips that can be adhered to or pushed into materials to be heated or into suitably sized holes drilled into such materials so as to measure the surface and/or internal temperature. The sensors 32 may be wired to a console 34 which displays and records the temperature at each sensor 32. Alternatively, the sensors 32 may be wireless and transmit a signal to the console 34. Typical sensors 32, as by way of example and not by way of limiting, include thermal couples, thermistors, or the like connected to a computer and/or a strip chart recorder console 34. It will also be appreciated that other temperature sensors, such as thermal imaging devices either used within the structure 30, or even outside of the structure, can be used.

A pressure measuring device, such as a manometer 36, may be positioned within the structure 30 so as to measure the internal pressure of the structure 30 during operation of the invention. As will be more fully described herein, in some instances, positive air pressure is desirable. However, in other instances, a negative pressure is established and maintained throughout the operation of the method of the present invention in order to prevent the dispersal of harmful biological and organic contaminants throughout the structure 30. The manometer 36 can be linked to the console 34 to provide the pressure information from without the structure 30.

One or more heaters 38 heat air to a predetermined temperature lethal to the organisms to be destroyed. For a more complete disinfection, the air temperature is preferably raised to at least about 155° F., with optimum results generally achieved with temperatures in the range of about 110° F. to 400° F.

Any suitable heater 38 may be used. A gas burning heating device, such as a conventional propane heater, is preferred as being particularly efficient in heating air. Typically, the propane heater is disposed outside of the enclosure and a fan or blower 40 is used to inject the heat into the structure through an inlet of the enclosure or enclosed structure. Any other heating arrangement, such as oil heaters, salamander heaters, electrical devices, solar heaters, and light emitting devices, may be used if desired. For example, instead of using a conventional propane heater, corn oil may be burned, a heater device running off of biodiesel fuel or the like may be used, etc. In some instances, such as when using an electrical heater, the heater may be disposed within the enclosure or structure, as will be more fully described herein. A hydronic heater may also be used, wherein a water or other liquid heater, which may be disposed on a movable trailer, heats the water or other liquid (such as glycol) which is then piped to heat exchangers within the building. Such a system provides many advantages, including the elimination of exhaust gas, prolonged heating, heating only specific areas, and using the hydronic hoses to radiate heat in difficult to heat locations, such as corners of rooms and the like.

Heated air from the one or more heaters 38 is directed through blower 40 (which may, if desired, be a component of the heater 38) which injects the hot air into the enclosed structure 30 through at least one inlet duct 42. Generally, a plurality of inlet ducts 42 will be used to achieve the optimum distribution of hot air throughout the enclosed structure 30. The inlet ducts 42 preferably include variable flow dampers and may be moved while the system is in operation to achieve uniform temperatures in all areas of the structure being treated, as sensed by sensors 32 and observed at console 34.

At least one outlet duct 44 is provided to allow the air to be removed from the structure 30. A blower or vacuum 46 is connected to the outlet duct 46 in order to remove air from the interior of the structure 30. Vacuum 46 may be used to create a negative pressure within the structure 30. Typically, this negative pressure is created before the heated air is introduced into the structure 30.

The removed air may be filtered, typically utilizing a high particulate arrestance filter, ULPA filter, or the like coupled with the vacuum/blower 46. Other filters such as charcoal filters or UV filters may be employed as well. Additionally, or alternatively, the air which is removed from the structure may be heated to very high temperatures so as to incinerate or otherwise neutralize the potentially harmful chemicals and microbiological organisms which have volatilized into the air. The filter or air scrubber 48 removes the remains of the organisms and VOCs from the air to prevent them from reaching the environment or being re-introduced into the structure 30.

Preferably, additional blowers or fans 50 are positioned within the structure 30 to aggressively move the air within the structure to further enhance the removal of harmful biological and organic substances by volatilizing the microbiological and chemical substances and aid in heat distribution.

The fans 50 may be positioned strategically within the structure 30 to move the heated air into all of the spaces which are intended to be heated. It is known that heat energy is stored at the atomic and molecular level. The hotter the atoms, the more active they are. If a hot object touches a cold object, heat will be transferred from the hot object to the cold object. By heating air molecules and blowing them into the treatment area, they give off heat to anything and everything they touch. If hot air is directed into a room, the hot air will give off heat to every item in the room that it comes into contact with. For heat transfer to occur, the objects must touch, there must be a physical connection. When the hot air molecules touch the wall surface, or other object, they transfer heat energy to the molecules on the surface of the wall or other object. The surface molecules then become hotter than the layered molecules below them. So, the surface molecules pass heat off to the next layer of molecules which then become hotter than the layer below it, so as to pass the heat off that layer and so on and so forth. This is called conduction, and is the primary method that heat is transferred in the process of the present invention. By increasing the movement of the air molecules, the efficiency of the heat transfer can be obtained. This is done with air flow, similar to the concept behind convection ovens that cook a roast in half the time of conventional ovens at the same temperature. Moving air transfers heat faster than stagnant or still air. Air always moves from an area with high pressure to an area of low pressure. The fans and the heaters of the present invention create a large volume of relatively high-pressure air. The air pressure in the heater and duct system is higher than the normal or atmospheric pressure. Thus, air flows out of the duct and into the treatment area. Areas of higher and lower pressure can be created inside the treatment area to create air flow patterns that are beneficial.

In a particularly preferred embodiment, the filtered air is re-directed through duct 52 into the structure 30, such as by linking duct 52 with inlet 42. Such re-circulation of heated air enhances the energy and thermal efficiency of the process and decreases the overall treatment time. Recirculating has been found to increase air circulation within the containment area of the structure 30. The re-circulated air may be blended with the heat processed air as it exits the heater, re-heated by the heater 38 or simply re-introduced by way of ducting into the structure 30.

A biocide may be selectively used depending upon the treatment of the building. For example, when treating insects, certain insecticides might be used. However, when treating the building for microbiological contamination, such as mold contamination, other biocides may be selected. The biocides may be sprayed, painted, or dispersed through the structure before the heating of the structure. Alternatively, or in addition to, biocides may be introduced into the heated air as it is forced into the structure. In this manner, the biocide is able to penetrate large areas of the structure and the air within the structure. For example, orange oil may be selectively placed within the structure, or introduced into the heated air. Orange oil and other citrus extracts, are very acidic. They can eat away at the insect's exoskeleton, as well as their internal membranes. In combination with heat, the orange oil has been found to be very effective in eradicating termites, and may be effective with other insects or organisms. The heat also serves as a catalyst for many biocides and fumigants. For example, the heated air can act as a catalyst for sulphural fluoride. This serves to reduce the total amount of fumigant used. It is believed that the elevated temperature increases the efficacy of insecticides, fumigants, pesticides and the like by increasing mobility of the insect and correspondingly greater pick up of insecticide deposits, by structural changes in the lipid layer covering the insect, allowing for increased penetration of the insecticide. Heat increases the physiological activity of the pests and in some cases the toxicity of the biocide. It is believed that similar phenomena may occur with microorganisms and the like. In any event, the amount of insecticide, pesticide, fumigant, desiccant, biocide, etc., can be significantly reduced when the temperature is elevated, such as 110° F. or more. The heat may also beneficially impact topical surfactants, including liquid, dust, and other forms of fumigants and insecticides and the like. In some instances, dessicants are also used, and the heat further serves to dessicate the building or area to be treated.

It will be appreciated by those skilled in the art that the present invention, as described above, can be used in a variety of scenarios. For example, in the event a building is infected with viruses or bacteria, such as a hospital, an individual's house which has been contaminated with a lethal virus or bacteria, an office building which has been exposed to bioterrorism or the like. The building may be simply de-gassed to remove VOCs and reduce the potential for SBS in the employees or occupants thereof. In such instances, when a dangerous chemical or microorganism is being removed from the enclosure, it will be appreciated that they cannot be simply released into the atmosphere. Instead, the filters and incinerators must be used to destroy, neutralize and contain these organisms and substances and prevent their release into the environment. However, in other cases, venting to the atmosphere is possible, such as when removing VOCs and the like.

The present invention, as described above, can also have various other specific applications. For example, in the northeastern portions of the United States, fuel oil is typically used to heat homes and other structures. Often, spills occur during the fueling process. These fuels are difficult to clean, and sometimes the fuel oil penetrates into building components. The present invention can volatilize and remove these spills.

As mentioned above, TCA residue left over from the cleaning process and interacting with mold in corks and the like is a tremendous problem in the wine industry. Structures can be heated and treated, in accordance with the present invention to volatilize this chemical from wine making facilities. Of course, the present invention will also kill the mold, and remove released spores and the like.

The air in the structure or removed therefrom can be sampled in order to determine if the level of contaminants in the heated air. For example, an outlet 54 may be installed in the ducting and a gas chromatograph, sometimes referred to an electronic nose, summa canister or a like device can be used to determine the levels of the contaminants before, during and after the heating process of the invention. It will also be appreciated that under certain conditions workers may be able to enter into the structure with such gas chromatographs, or other sensing devices to test the air, the building components, etc. during the treatment. This can be used in determining the period of time necessary to treat the structure. When the contaminants, such as VOCs has fallen below acceptable limits, the process can be terminated.

Figure 3:
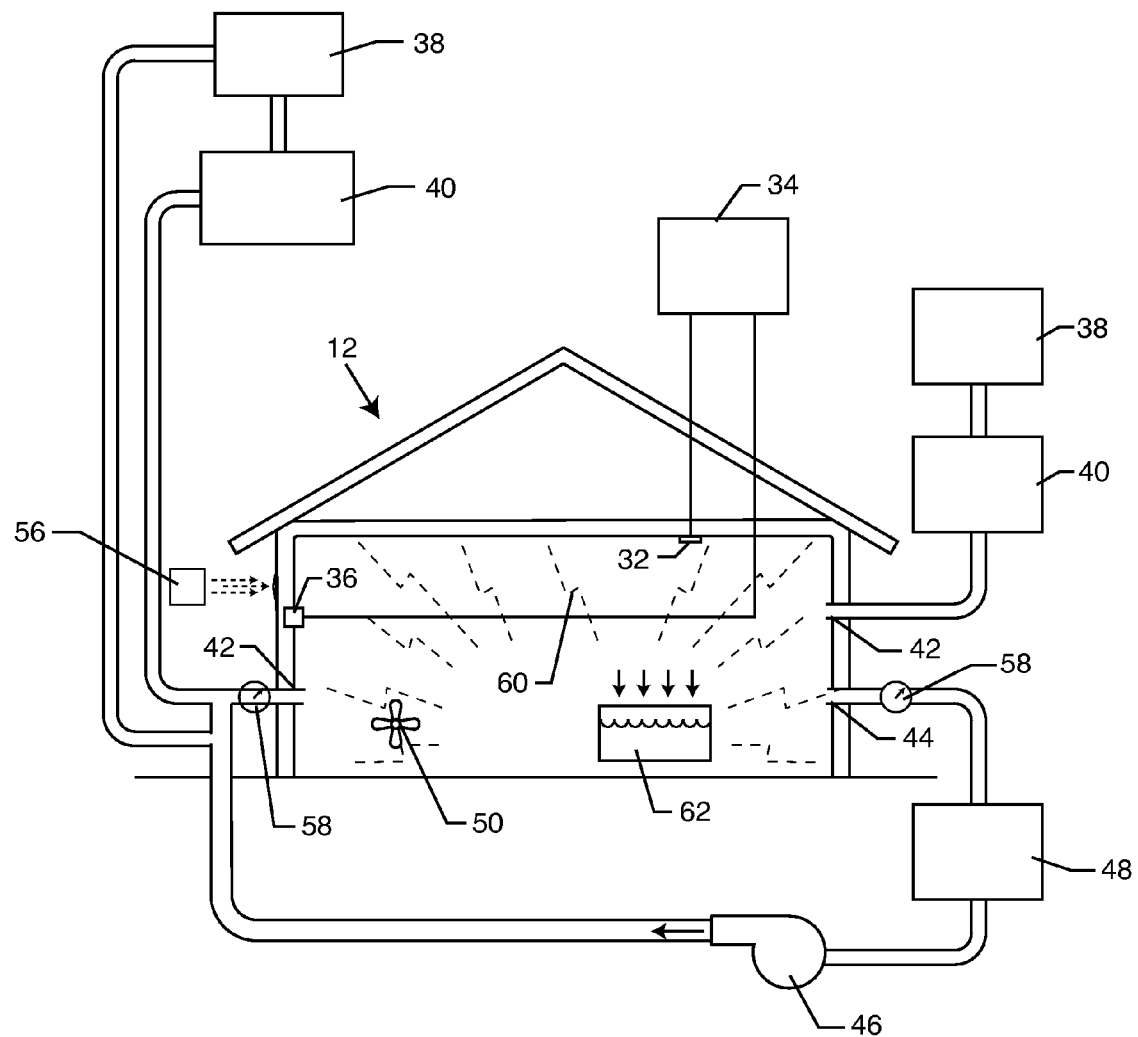
FIGS. 3-9 are schematic diagrams showing components of other embodiments of the present invention, installed for treatment of a building.

With reference now to FIG. 3, yet another embodiment is shown. A temperature sensor 32 may be positioned within the structure to monitor the temperature of the structure 30. If the temperature sensor 32 is disposed within the structure 30, it is typically inserted into the structure 30 itself, such as by drilling a hole into a wooden beam or the like and inserting the temperature sensor 32 therein so as to monitor the temperature within the supports of the structure itself. The temperature of the structure 30 may also be monitored using an external temperature sensor 56. Such sensor may be placed on a window, for example, or, as illustrated, comprise a laser temperature sensor wherein a beam of laser light is directed at the structure and used to determine the temperature of the structure 30. The temperature of the structure 30 can also be monitored by a sensor 58 at the ingress to the structure or at the egress duct of the structure.

The system may also incorporate the use of a radiation emitting device which can emit microwave, radio waves or infrared emitting radiation 60 to heat the air within the structure. Such a device may be used in association with the gas burning heating device, or placed within areas of the structure to heat the structure directly from within. Various spectrums may be selected so that the electromagnetic device may also serve to kill organisms, such as by emitting ultraviolet light 60 or the like. Another radiation emitting device that could be used is an electron beam emitting device, such as those offered by Electron Beams, Inc. Electron beams have been found to cleave chemical bonds or seal others, such as to disrupt a virus or bacteria's genes. Electron beams can break carbon bonds and thus sterilize the air or area or the contaminated area. One such radiation emitting device can be placement of ultraviolet lights, which are known to cleave chemical bonds and kill viruses and bacterial. Such radiation emitting devices, such as ultraviolet lights, can also be incorporated into an outlet chamber or filter system such that airborne microbes and harmful chemicals can be destroyed before being filtered, recirculated into the structure to be treated, or even released into the environment.

Figure 26:
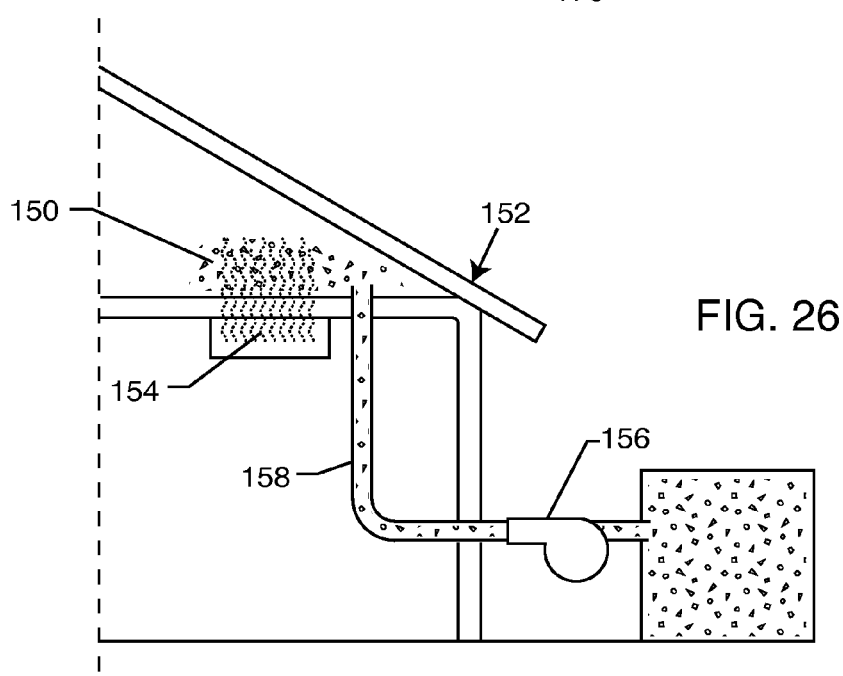
FIG. 26 is a schematic diagram illustrating treatment of a portion of a structure using a metal-based material and electromagnetic waves in accordance with the present invention.

The electromagnetic device may be a radio wave generator or a microwave radiation generator. Microwaves, or even radio waves at certain frequencies and intensity, can serve to heat the structure and/or kill insects and other biological organisms. With reference to FIG. 26, in addition, or alternatively, metallic-based products 150 could be injected, painted, aerosolized, etc., into a building or enclosure 152 and then, using radio waves 154, they are heated. The temperature and the metallic material itself would be synergistic in killing the targeted organisms. Such methodology could be used for treating mold, bacteria, other organisms or possibly even insects. The metallic-based materials could include zinc oxide or titanium. Other conductive materials, such as carbon-based materials, such as nanoparticles or barium metaborate could possibly be used. This provides a targeted, non-invasive treatment for disinfection or pest eradication. As illustrated in FIG. 26, the metallic-based material, such as a metallic powder, paste, liquid, etc. is applied to the area of concern. In the case of the metallic-based material being a powder substance, the metallic-based material 150 can be pumped by means of a blower 156 through a conduit 158 into hard-to-reach places, such as between walls, interstitial areas, between a roof and ceiling, between eaves, and the like. Of course, the metallic-based material may be applied manually, or by other means, to contaminated areas. As mentioned above, the metallic-based material could be painted, aerosolized, etc. to the area of concern. For example, the metal-based material, or other appropriate material capable of being heated by the electromagnetic radio waves or the like, can be injected into interstitial areas, voids, spaces and other areas which are otherwise difficult to treat. The process allows the use of heat in a more directed way and the biocides left behind would give a residual benefit for years to come. For example, the metal-based material can serve to kill the insects or microorganisms. When insects come into contact with such material, the material can scrape and cut the exoskeleton of the insect, causing it to die.

In this regard, the methodology of the present invention can be utilized to treat vegetation to eradicate infestations without the use of poisons. For example, crops may be dusted with a metal-based dust. When the dust is heated utilizing radio waves, the infestations may be eradicated without harming the underlying vegetation. The process also relates to treating trees having beetle infestations. The portion of the trees infested may be dusted with a metal-based dust which is later heater with radio waves to eradicate the infestation.

The air which is heated and introduced into the structure can be selectively devoid of humidity and moisture as well as carbon dioxide or carbon monoxide. Accordingly, a dehumidifier 62 may be placed within one or more areas of the structure in order to remove the moisture from the air therein. The removal of moisture is particularly useful when treating for insects or toxic mold and the like. In one embodiment, moisture is added to air initially so as to enhance the treatment, and then removed towards the end of the process, such as using the illustrated dehumidifier 62, so that the contaminated area and structure are dry. Drying the contaminated area and structure kills the toxic mold and prevents other mold and fungus from growing in the future.

Figure 4:
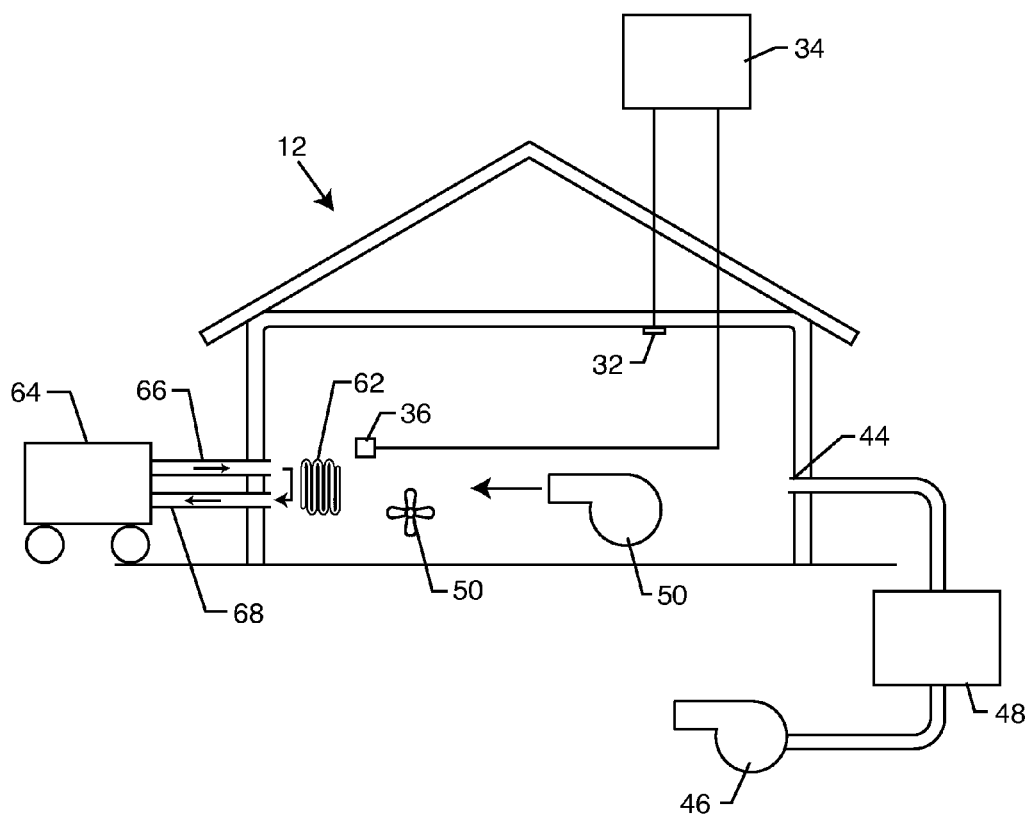

With reference now to FIG. 4, another embodiment of the invention is illustrated which is similar to that described above. However, instead of using an external heater, such as a propane gas tank heater, with inlet ducts, this embodiment utilizes a liquid-to-air heat exchanger device 62 disposed within the enclosure. A heating device 64, preferably a device which is movable or placed on a trailer or the like, heats a liquid, such as water, oil, etc. The heated liquid is then transferred via an inlet conduit 66 into the heat exchanger device 64. Radiator-like fins, fans, etc. can be used to force air over the heat exchanger 62 and cause the air to be heated as it comes into contact with the exterior surfaces of the heat exchanger 62. The now cooler liquid is then returned to the heater 64 through an outlet conduit 68. The conduits 66 and 68 can be linked to multiple heat exchangers 62, or multiple inlet and outlet conduits 66 and 68 can extend from the heater 64 to each heat exchanger 62 so as to sufficiently heat the air within the structure 30. A benefit of this embodiment is that the preparation of the structure 30 is minimized by eliminating the need for ducts and the like. As previously described, however, the system still preferably includes blowers or fans 50 for aggressively moving the air within the structure 30, temperature probes and pressure sensors 32 and 36, as necessary, for monitoring the appropriate temperatures and desired pressure.

As discussed above, when treating structures 30 having dangerous microorganisms or chemical substances, a negative pressure can be created with a blower 46 attached to an outlet vent 44. An incinerator or filter 48 can be used to neutralize and destroy these organisms and substances as they are pulled from the structure 30. It will be understood, however, that in other instances there is no need for an outlet duct or conduit 44, filter 48 and blower 46. Instead, a positive pressure is built up within the structure 30 due to the heating of the air by the heat exchanger 62, and the aggressive movement of the air by the blowers and fans 50. In this case, an outlet in the form of an open window or the like can be used to exhaust the heated air from the structure 30. Such may be the case, for example, when treating buildings for volatile organic compounds or the like which do not present a hazard when vented to the atmosphere. However, in other instances, such as when dealing with harmful microorganisms and allergens and the like, it is preferable to filter such air so as to eliminate the spreading of the contamination to other areas of the structure, as well as to vent filtered and clean air into the environment.

Figure 5:
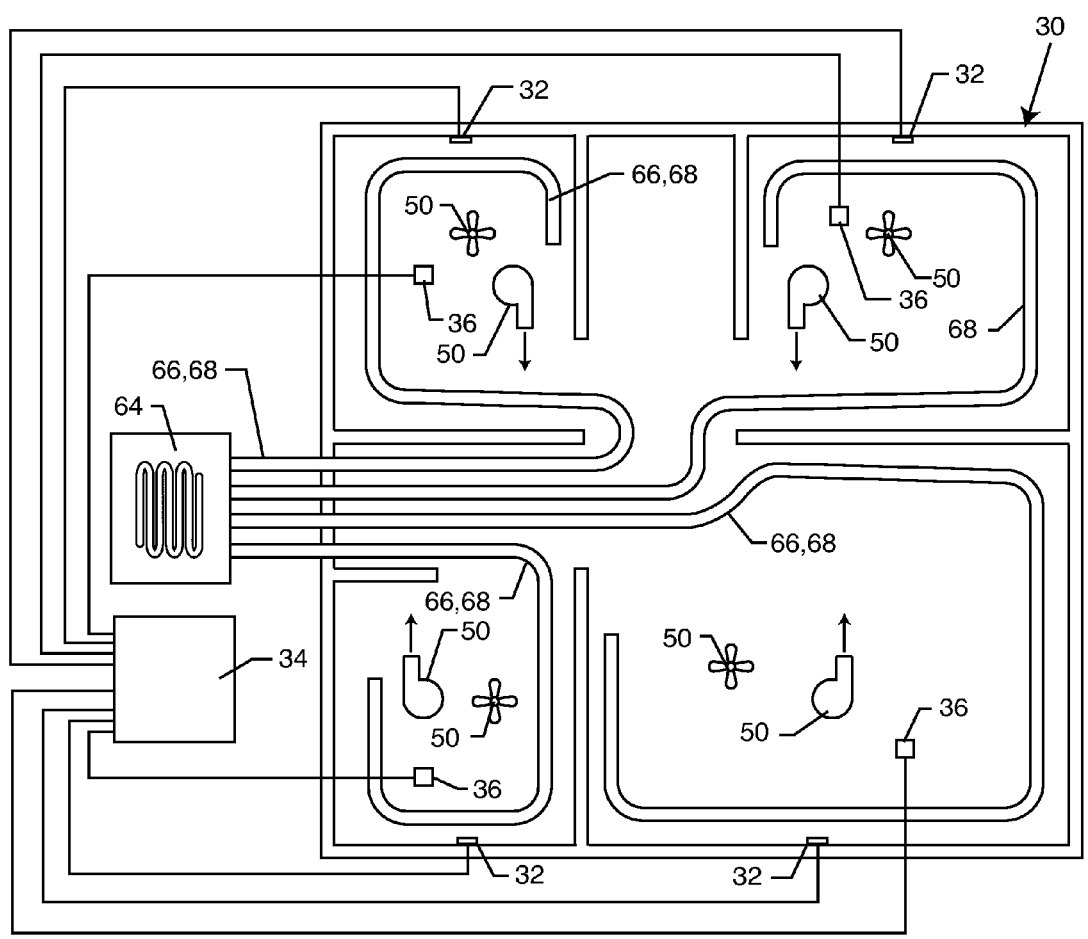

With reference now to FIG. 5, in yet another embodiment of the present invention, a heater 64 is either positioned outside of the structure or within the structure. Hoses 68 extend from the heating apparatus 64 and are selectively positioned within the structure 30, such as in corners and other areas which can be shielded from moving heated air and otherwise difficult to heat. The hoses 68 may either carry heated air, or more typically heated water, so that the air in the corners and other difficult to access locations are heated by means of radiant conductive heat. In fact, the entire structure 30 could be heated in such a manner, preferably with blowers 50 and the like within the structure to aggressively move the air throughout the structure to more effectively heat the structure.

Figure 25:
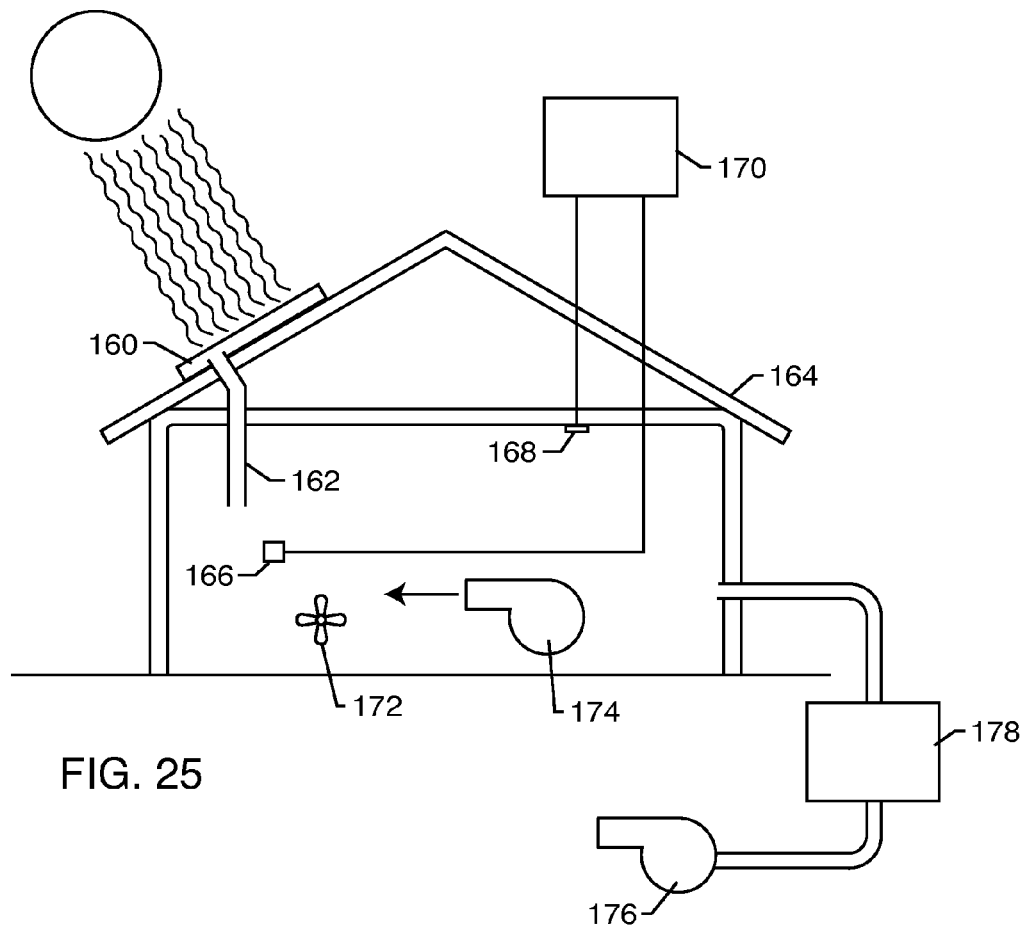
FIG. 25 is a schematic diagram illustrating treatment of a structure utilizing a solar heater device, in accordance with the present invention.

With reference now to FIG. 25, such hydronic heating can be accomplished by means of a solar collecting panel 160 placed at a location, such as the roof of the building, so as to collect solar energy therein. Fluid, such as water or glycol or the like, is pumped through tubing 162 into the structure 164 to be treated. The fluid may terminate in a heat exchanger device 62, as illustrated in FIG. 4, or be re-circulated through one or more elongated tubes selectively placed throughout the area of the structure 164 to be treated, as illustrated in FIG. 5. Pressure sensing devices 166, temperature sensing devices 168 and the like may be connected to a console or recorder 170 so as to monitor the pressure and/or temperature within the structure 164. Moreover, fans 172 are positioned within the structure 164 so as to aggressively move the heated air to the areas intended for treatment, and so as to increase the efficacy of the heat transfer.

In some cases, the heat generated from the solar panel/collector 160 is not sufficient to raise the temperature to the necessary level to kill the harmful microorganisms or insects. Accordingly, heat may be introduced through other devices 174, positioned within or without the structure 164, as described above, so as to raise the heat to the necessary level within the structure 164 in a synergistic manner in conjunction with the solar collector panel 160. In a particularly preferred embodiment, the air within the structure 164 is circulated, such as with blower 176, through a filter or air scrubber 178, which may be positioned within or without the structure.

Figure 6:
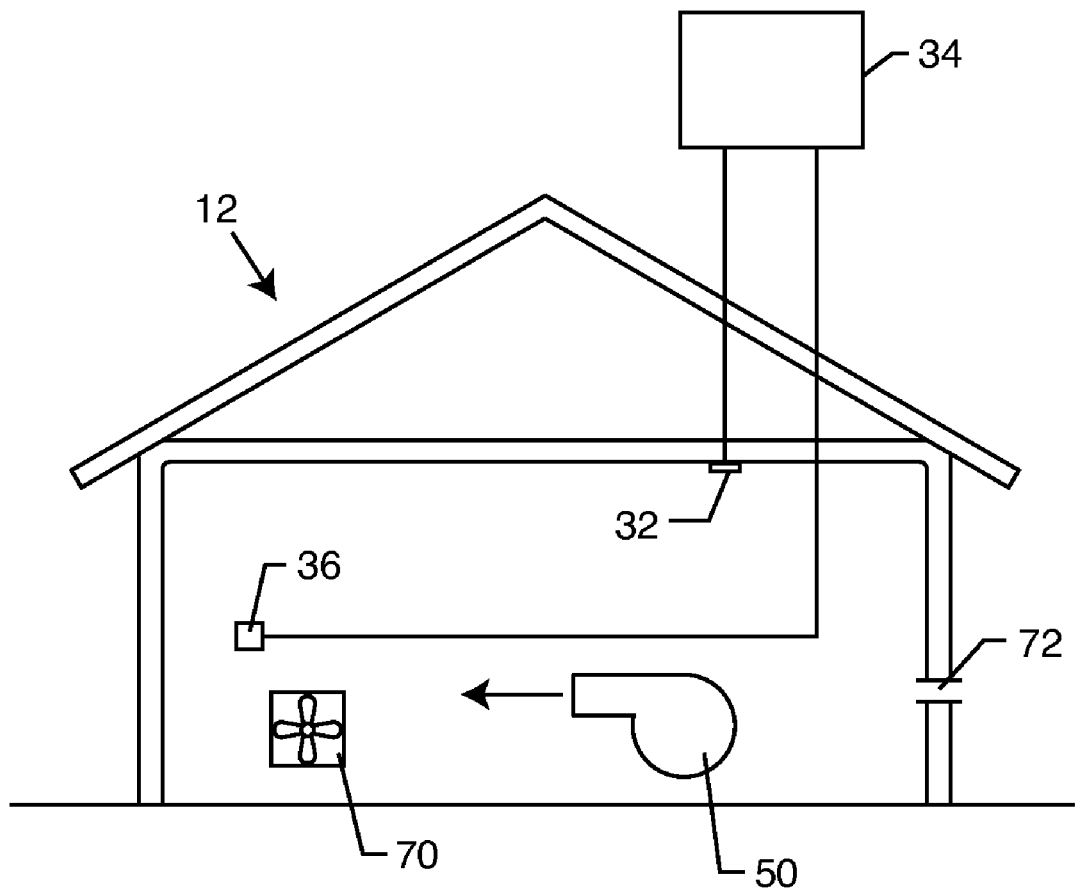

With reference now to FIG. 6, yet another embodiment is shown which is similar to that described above. However, instead of an external heater, this embodiment utilizes an internal electric space heater 70. In this case, one or more electric heaters 70 are selectively positioned within the structure 30 and serve to heat the air therein. Blowers and fans 50 or the like can be used to aggressively move the air past the heating coils of the heater 70 to heat the air, as well as volatilize certain chemicals into the air. By increasing the temperature, and the air movement, the vapor pressure is increased. By increasing vapor pressure, certain chemicals can be volatilized into the air and removed from the building structure 30 and other fixtures or components within the building. The pressure and temperature sensors 32 and 36 are used and connected to a console 34 or otherwise monitored to ensure either the proper negative or positive pressure, as well as the proper temperature range needed for the particular structure 30. In the embodiment illustrated in FIG. 6, there is no outlet duct or conduit or filter. Instead, the outlet 72 is an opening in the structure 30, such as an open door, window, etc. It will be appreciated by those skilled in the art that this presents a significant labor savings when preparing the structure. It will be understood, however, that in most cases it is preferable to filter the air either by circulating the air through a filter within the portion of the structure being treated, positioning a filter or air scrubber within a recirculation loop, or passing the air through a filter or air scrubber prior to venting it to the atmosphere.

Nonetheless, in the embodiments illustrated in FIGS. 4-6, with the heat exchanger device 64 and internally placed heater 70, any number of the steps and components illustrated and described with respect to previous Figures can be implemented, as needed. Thus, the entire structure 30 can be sealed and inlet and outlet ducts incorporated. Either positive or negative pressure can be utilized. When dealing with harmful substances, a negative pressure and filter or incinerator 48 are used. However, in many cases, the doors and windows of the building can be closed and sealed the building sufficiently to create an enclosure whereby the air can be heated to the necessary temperature to either kill the microorganisms, pests, or cause the chemical substances to be released into the heated air for removal.

In some instances, certain areas of the structure 30 will be cleaned and pre-treated, such as by applying a biocide (such as boric acid, or the like) scraping and removing sections of walls or flooring having toxic mold and the like, etc. In other cases, these steps may not be necessary.

In some cases, the air within the structure 30 need only be heated to between 110° F. to 200° F. However, in other cases, the required temperatures are much higher, such as 200° F. to 400° F.

Figure 7:
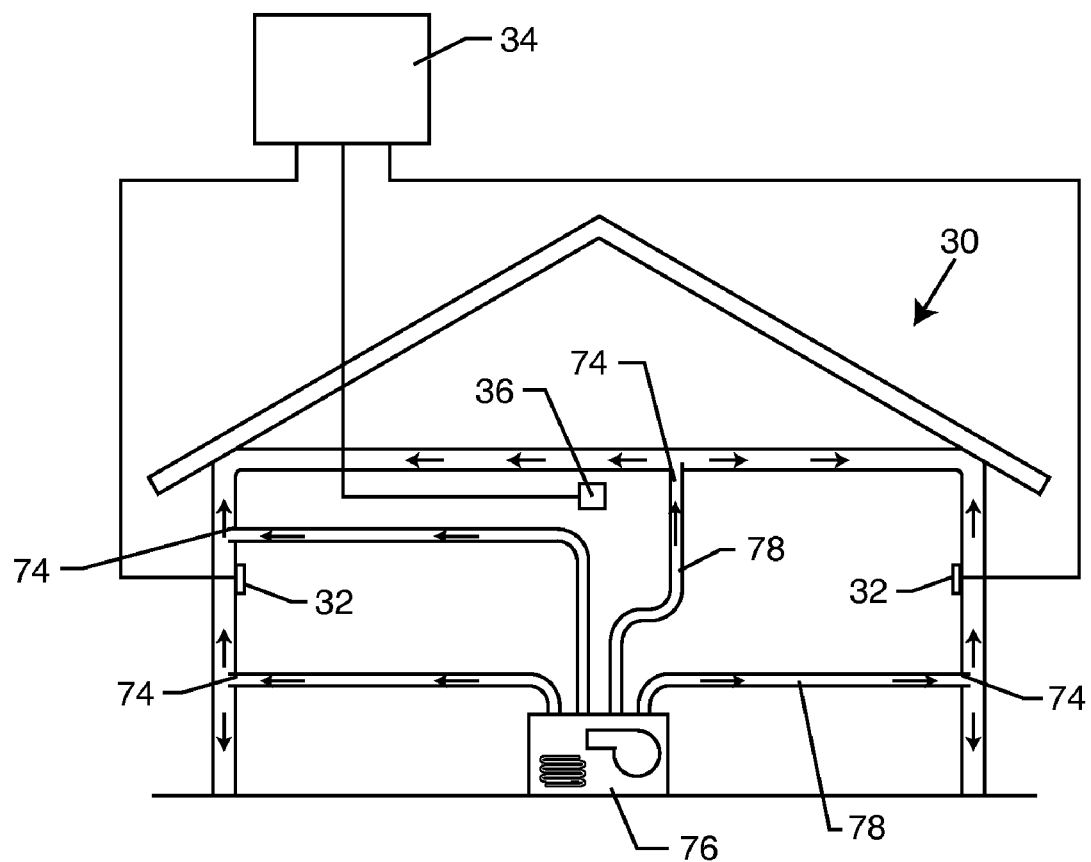

With reference now to FIG. 7, in another embodiment of the present invention, heated air under positive pressure is injected into interior spaces of the structure. For example, holes 74 may be drilled into the walls of the structure 30 and then heated air under positive pressure is injected therein. Air blowers/heaters 76 having hoses 78 extending therefrom, such as the John-Don DIRECTED AXIAL ADAPTER, DIRECT-IN AIR MOVER ADAPTER, and DRI FORCED DRYING SYSTEM could be used. Preferably, such air blowers/heaters have hoses attached to multiple outlets so that the air can be directed to several specific holes 74 in the wall. This can be used, for example, to heat and kill pest infestations, such as termites, or used in mold abatement and the like between walls.

Figure 8:
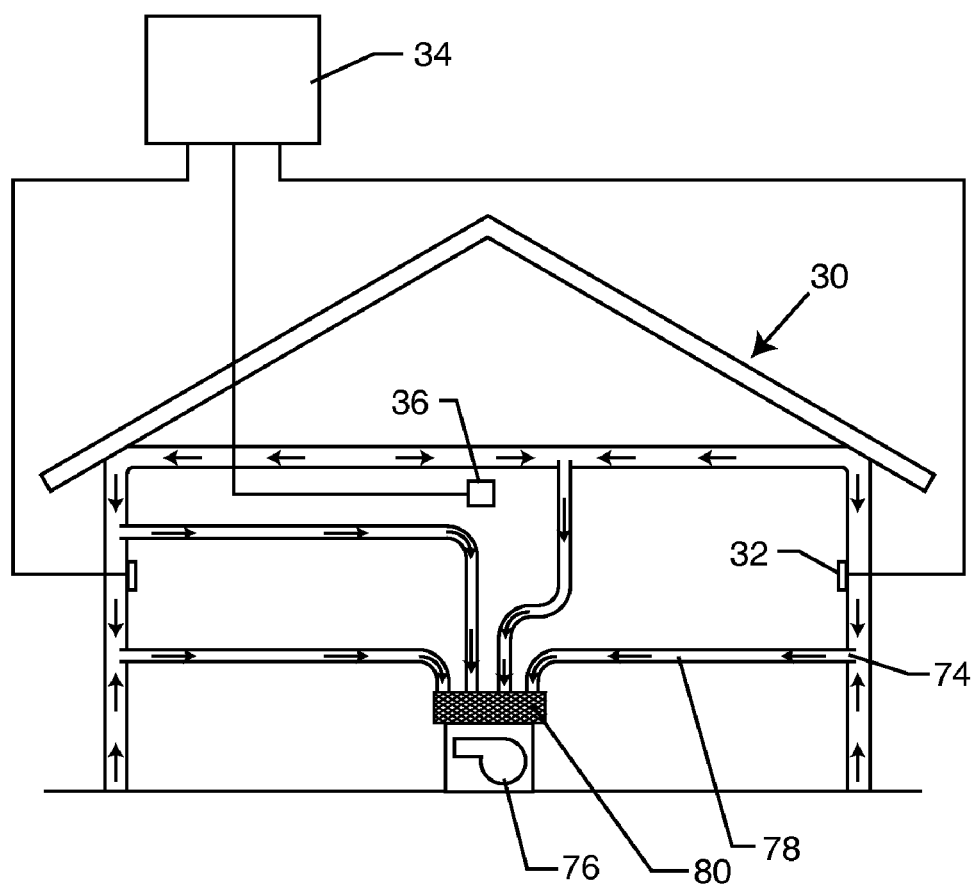

With reference now to FIG. 8, in certain instances, it is desirable to create a negative pressure in the holes 74 that have been accessed or created in the wall or other portion of the structure 30. For example, in the situation of mold or fungi contamination, it would be desirable to capture any aerosolized spores or other material so as to prevent the infestation from contaminating other portions of the structure. As illustrated in FIG. 8, in such a case a blower/pump 76 having hoses 78 extending into the apertures of the wall sucks air from the apertures, and thus the space between the walls and the like. A filtration unit 80 may be connected to the hoses before the air is drawn through the pump/blower device 76. The filtration unit 80 may include HEPA or other filters, radiation devices, etc., for filtering the contaminants from the removed air.

Figure 23:
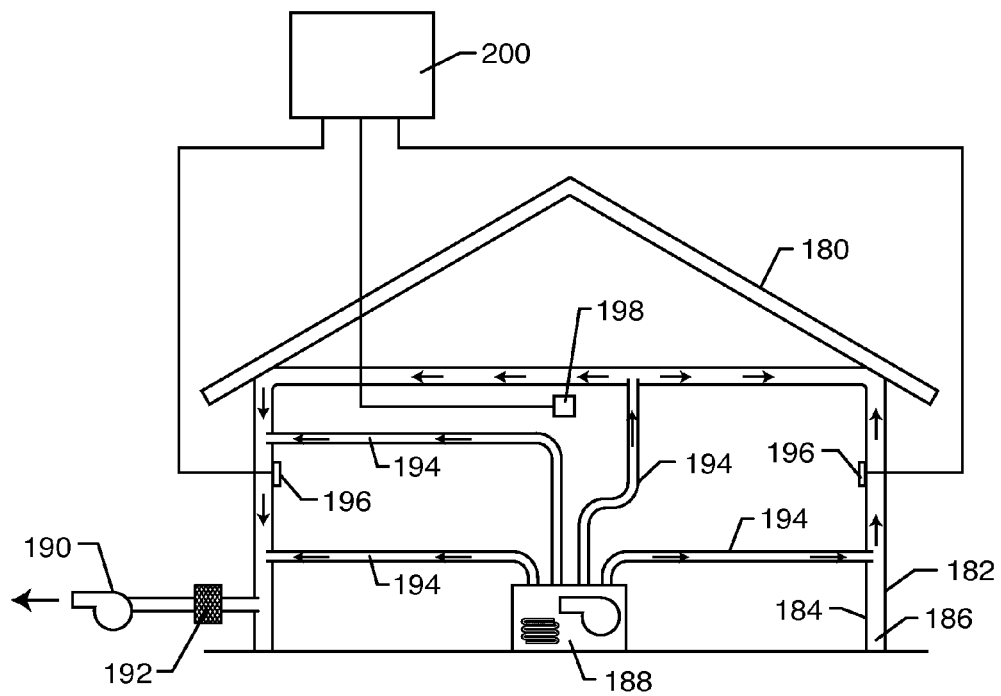
FIGS. 23 and 24 are diagrammatic representations showing internal spaces between a wall of a structure treated in accordance with the present invention.

With reference now to FIG. 23, a structure 180 is illustrated having at least a portion thereof being treated in accordance with the present invention. More particularly, walls 182 and 184 having a space 186 therebetween is being treated. This may be due to water damage and mold infestation, insect infestation, or the like. A heater 188 pumps heated air into the space and voids 186 between the walls 182 and 184. This may be done in a variety of ways. For example, apertures can be formed in the walls and the entire room treated, such that the heated air enters into the apertures and in between the walls 182 and 184. An aperture may be formed, or an existing aperture selectively used, and coupled to a pump or blower 190 so as to remove the air from within the space 186, preferably through a filter 192 or air scrubber. This serves to remove the existing cooler, and possibly damp, air from within the space 186 of the walls 182 and 184, and facilitating the entry of the heated air into the space between the walls as well as a vigorous air flow therein. In a particularly preferred embodiment, one or more tubes or conduits 194 extend from the heater and blower device 188 and into existing or formed apertures in the walls 184 so as to introduce the air therein. Temperature probes 196 are used to monitor the temperature of the space 186 between the walls 182 and 184 to insure that the lethal and effective temperature is achieved for the predetermined amount of time. One or more pressure sensors, such as a manometer 198, may also be used to measure structure within the structure 180, or even within the space 186 between the walls 182 and 184. The sensors may be connected to a console or recorder 200 which monitors the pressure and/or temperature in the areas being treated.

Figure 24:
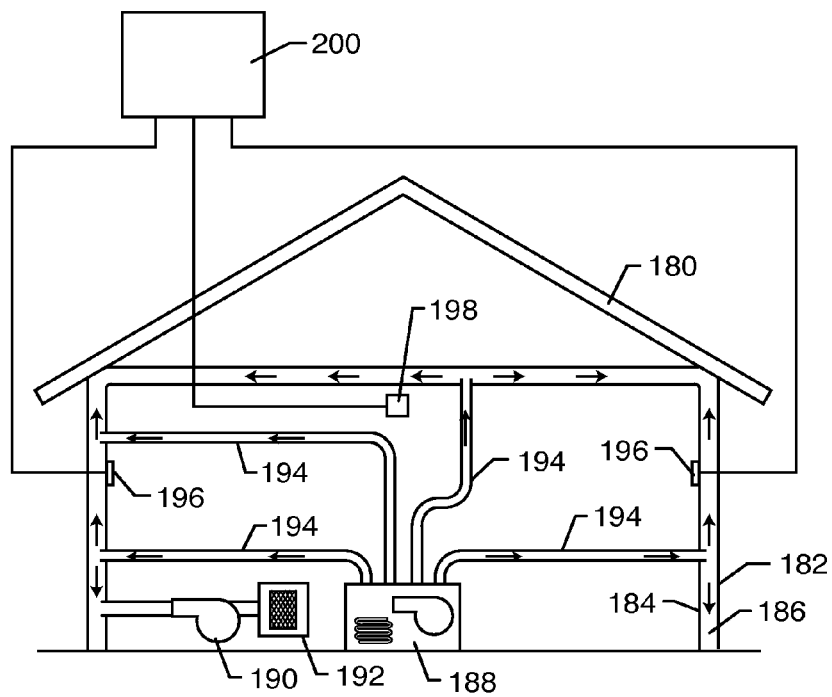

With reference now to FIG. 24, an embodiment similar to that illustrated in FIG. 23 is illustrated, but instead of pumping the air through a filter 192 into the environment, the pump/blower 190 is disposed within the structure 180 so as to pass the treated air through filter 192, which is then emitted into the structure 180 itself so as to be re-circulated and treat the one or more rooms or other areas of the structure 180. It will also be understood that having such inlets and outlets formed in the walls 182 and 184 allows the control of the pressure within the space 186 between the walls 182 and 184. For example, it may be desirable to initially create a negative pressure such that the cooler and infected/contaminated air is quickly removed while the heated air is introduced within the space 186. However, it may later be desirable to increase the incoming pressure of the heated air from the heating device 188 so as to create a positive pressure of heated air within the space and voids 186. In any event, it is preferred to remove and pass the treated air through a filter 192 so as not to infect and contaminate other portions of the structure 180 or even the environment, as discussed above.

Figure 27:
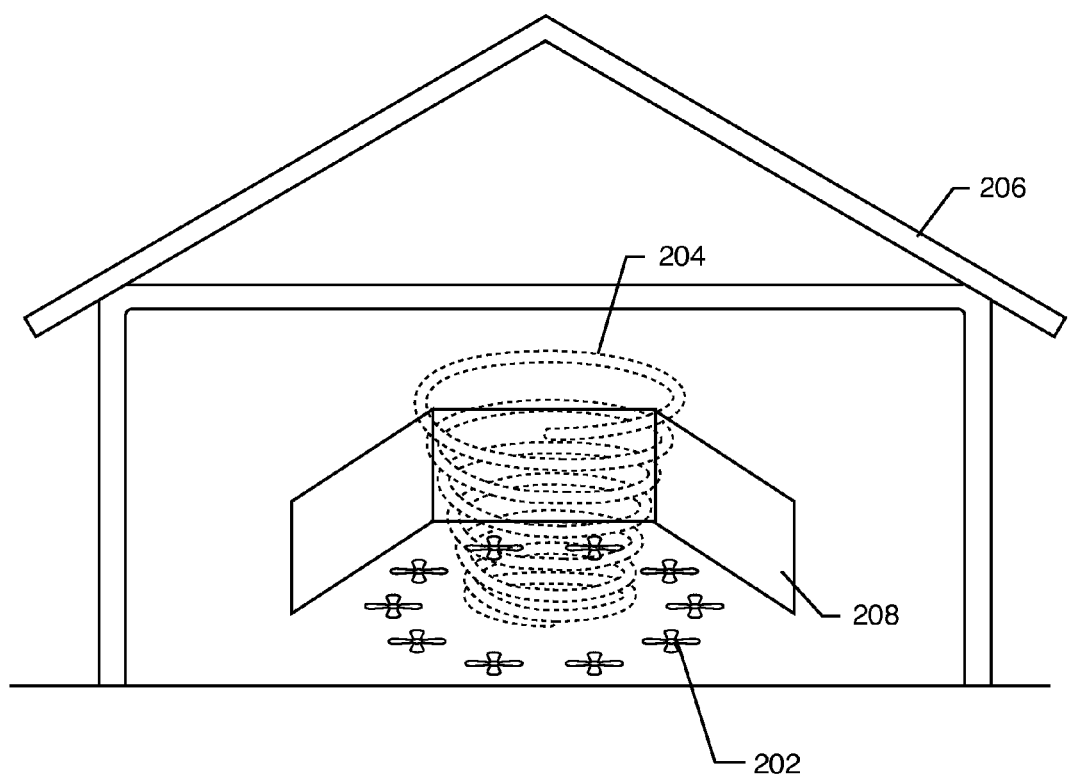
FIG. 27 is a schematic diagram showing a structure being treated in accordance with the present invention by means of a heater and a plurality of fans forming a wind cyclone within the structure.

With reference now to FIG. 27, in yet another embodiment of the present invention, a plurality of fans 202 are positioned in a configuration, such as a circular configuration, serve as to create a whirl-wind, cyclone, or vortex of air 204. This may be done immediately adjacent to or surrounding a heater 208. Creating such a cyclone 204 with the plurality of fans 202 results in a very aggressive movement of air within the portion of the structure 206 being treated. As described above, movement of air within the treatment area is very important so as to maximize heat transfer between the air and the contaminated portions of the structure 206, as well as to assist in any aerosolization of allergens, microbiological contaminants, and the like. Such a fan 202 arrangement and resulting cyclone 204 could be used in any of the embodiments described herein so as to improve efficacy of treatment.

With continuing reference to FIG. 27, the present invention also contemplates the use of an infrared heater 208. The infrared heater 208 can be powered with either propane (or any other applicable fuel source) or electricity. The infrared heater emits infrared rays, which serve to heat the structure components adjacent thereto and the surrounding air. Typically, the BTU output of the infrared heater 208 is relatively low, thus the creation of the cyclone 204 converts the infrared heat to convective heat and assists in delivery of the heat to the targeted areas.

It will be appreciated by those skilled in the art that more than one heating apparatus can be used in association with the present invention. For example, a building may be brought up to a certain temperature using a first type of heating device. For example, an infrared heater, a hydronic system, a solar-powered heat generation/transfer system or the like may be used to elevate the temperature within the structure to a first level. This level may not be enough to completely decontaminate and kill the microorganisms and insects in question. Thus, a second heating device, such as a gas-powered blower, electrical heater, gas heater, or the like, may be used either within or outside of the structure so as to heat the air within the structure to a second higher temperature which is more lethal to the microorganisms and insects. It will also be understood that multiple heating devices may be used in order to heat the structural portions of the structure in a different manner. For example, hydronic heating or the like may be used to heat lower portions of the structure, corners, etc. while a gas or electric powered heater is used to heat the larger interior spaces of the structure.

Figure 9:
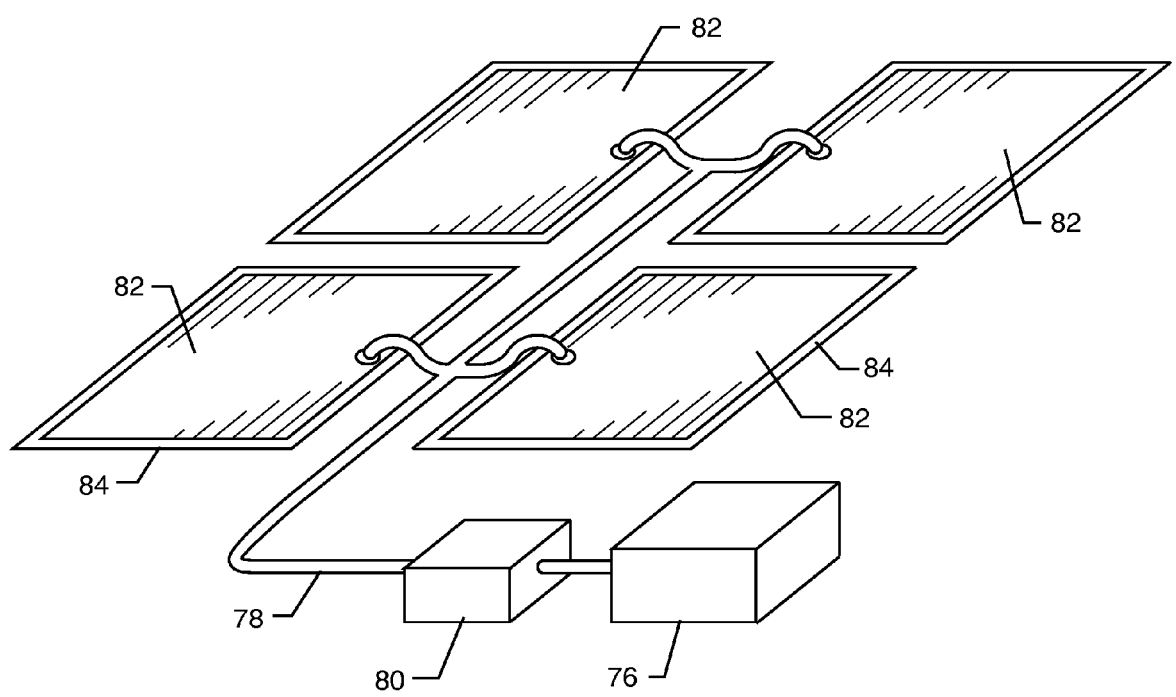

With reference now to FIG. 9, when treating concrete slabs, soil or the like, paneling or tarps 82 or the like may be placed over the floor or soil. Typically, the panels or tarps 82 are sealed, such as using 84 tape or the like. Hoses 78 extend from the panels to a heater/blower device 76, which can either inject air into or draw air from the areas directly under the panels 82 so as to treat the floor or soil. Typically, heated air will be injected under the panel 82 so as to treat the area of the floor, concrete slab or soil immediately under the panel, which serves to trap the heat and pressurized air so as to kill the microorganisms, pests, or destroy other contaminants. The VAC-IT 5 POINT PANEL SYSTEM offered by John-Don is particularly suited for such a procedure. However, in some cases, it is desirable to create a negative pressure using the blower device 76, such as when treating flooring and the like contaminated with mold. In such instance, the drawn air through the hoses 78 is passed through a filtration unit 80 to prevent spores, contagions and allergens from entering the atmosphere and contaminating other areas.

Figure 10:
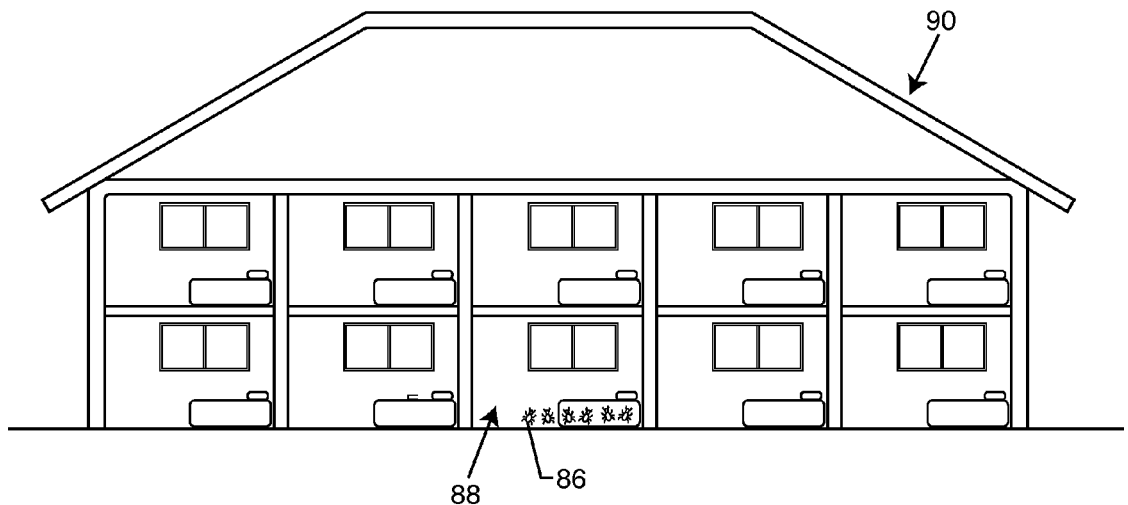
FIGS. 10-13 are schematic diagrams of a multi-unit building having at least one room infested with pests, such as bed bugs.
Figure 11:
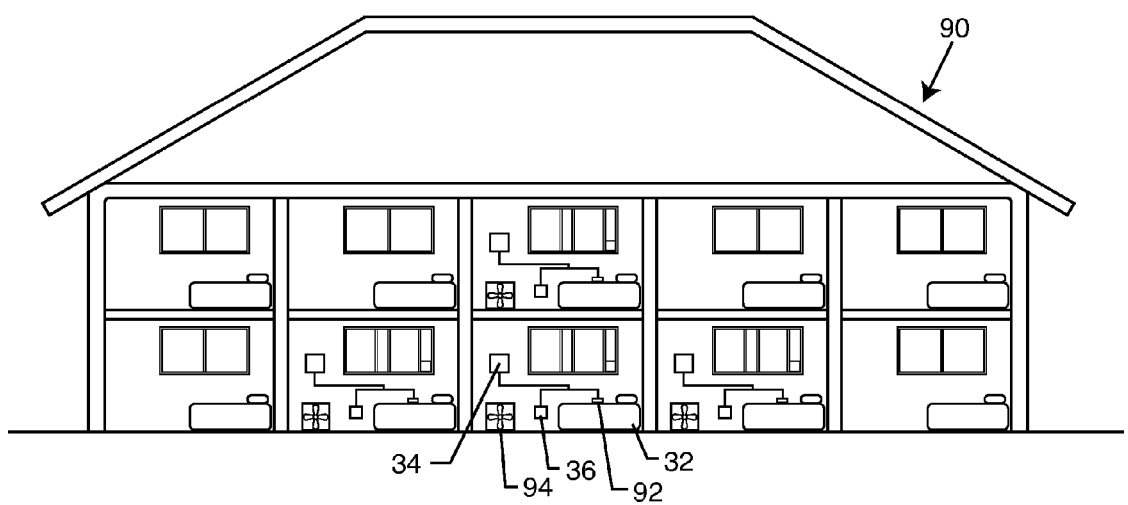

With reference now to FIGS. 10 and 11, there currently exists a significant problem with pests, in particular fleas, head lice or bed bugs 86, infesting a room 88 of a multi-unit building 90, such as a hotel or apartment building. Pests such as fleas and head lice can be introduced by the individual staying in the room 88 or their pets. Bed bugs, blood-sucking parasites, can be introduced in a variety of ways, such as birds or bats nesting in the eves of the building 90, etc. These bugs 86 find their way through cracks and crevices in the building and aggressively pursue hosts, such as sleeping humans. As discussed above, bed bugs hide in cracks and crevices during the day and come out at night to feed. Such bugs are not limited to the bed, but can be found in stuffed furniture, behind loose wallpaper, under carpet, behind picture frames and in electrical outlets, etc. Thus, merely cleaning or destroying the bed or bedding will not resolve the problem. Fumigating presents many drawbacks, particularly in a hotel setting. Although the entire building 90 could be treated, this presents a serious financial drawback for the several days in which the building must be prepared and treated.

Accordingly, the present invention can be used to treat a single room 88, or its adjacent rooms, as illustrated in FIG. 11, to eradicate the pests. The room 88 is prepared by placing temperature probes 32 at selected locations within the room 88, such as between the mattresses of the bed 92, and other known bed bug harborages, including under cushions, stuffed furniture, under carpeting, etc. Heaters 94 are disposed within the room or the necessary ducting is implemented. A console 34 or the like can be used to monitor the operation of the temperature probe 32 and heater 94, as necessary.

Prior to heat treatment, cracks and crevices and other bed bug harborage areas can be dusted with biocides or diatomaceous earth or silica aerogel, which can adversely affect the cuticle or exoskeleton of the bugs and make them more susceptible to heat treatment. The room 88 is then heated to a predetermined temperature, such as 140° F., for the necessary time. Three hours at this temperature typically kills the bed bugs 86.

Although the bed bugs may only be known to be present in one room, such as when a hotel guest complains of bed bug bites, it is most desirable that the rooms surrounding the infested room 88 also be treated. This is due to the fact that bed bugs and other insect pests can crawl through crevices, along electrical lines, etc., to reach areas of lower temperature and safety. Thus, if the heaters 94 are disposed in the adjacent rooms 66-70, so as to heat these rooms as well, the bed bugs 86 will be destroyed, even if crawling along plumbing lines, electrical lines, air ducts, etc. However, this still enables the selective treatment of as few as a single room, and perhaps as many as four to six rooms of the entire hotel or apartment complex to completely eradicate the bed bugs.

After treatment, all crack, crevices, mattresses, etc., are vacuumed and inspected to remove the dead bed bugs and eggs. The cracks and crevices are then sealed, such as using caulking material or the like, to prevent future infestation.

Although the rooms can be sealed, and inlet and outlet ducts provided, as described above, due to the relatively lower temperatures (130° F.-140° F.) and the non-toxic nature of the killed insects, the rooms need relatively little preparation other than the closing of windows and sealing of door jambs and the like and the installation of the heater 94 and temperature probes 32. Once the method of the present invention has been used to eradicate the bed bugs, this can typically be done in less than one-day, with no toxic or adverse affects to future customers of the hotel or apartment. Of course, it will be appreciated, that the methodology of the present invention can be used in a multi-room building, such as a hotel, office building, or the like not only with respect to bed bugs, but also other pests and contamination such that only a portion or even as few as a single room of the building can be treated.

Figure 12:
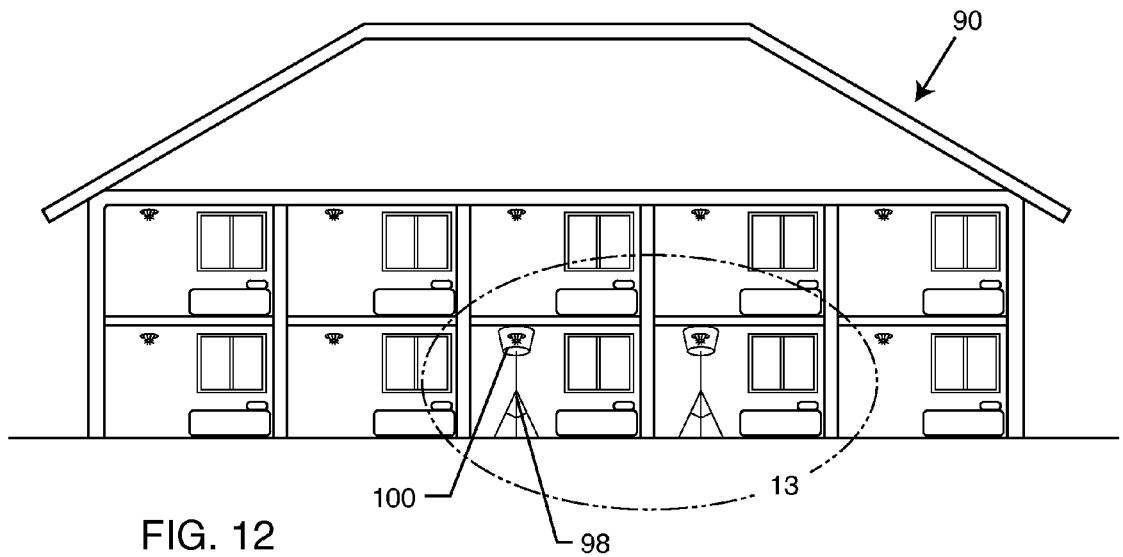
Figure 13:
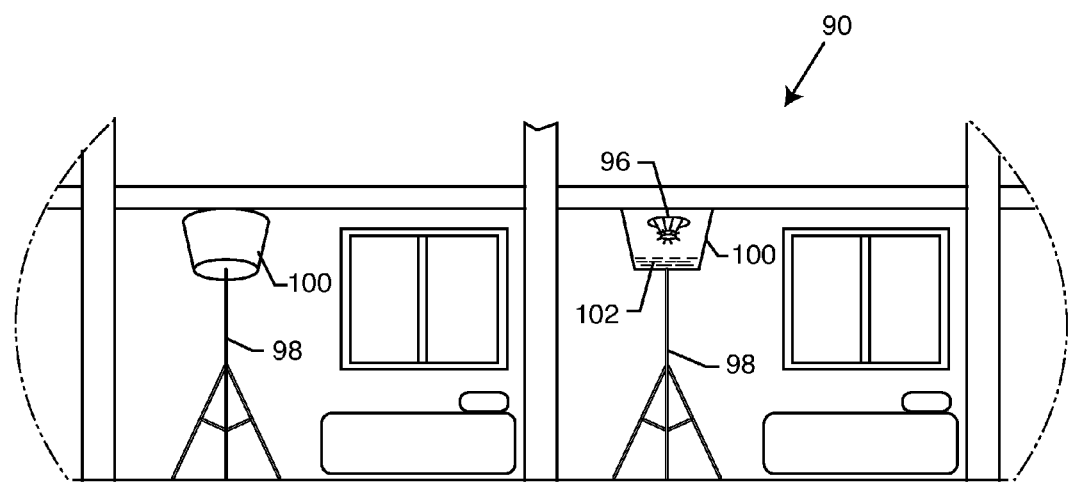

With reference now to FIGS. 12 and 13, a problem that can be encountered when conducting the process of the present invention is when only a portion of a structure 90, such as a single or less than all of the rooms of the hotel or the like, are treated. In such commercial buildings, fire suppression systems are required by code. Such systems are activated when the internal temperature exceeds a predetermined level. Such a level can be exceeded using the temperatures of the present invention. Accordingly, sprinkler heads or other such sensors 96 of the fire suppression system in those rooms or areas 88 to be treated are shielded from the heat. One manner of doing so is to support 98 a bucket or bag 100 containing dry ice or other cooling agent 102 directly over the sprinkler head. The room can then be heated and treated without activating the fire suppression system.

Figure 14:
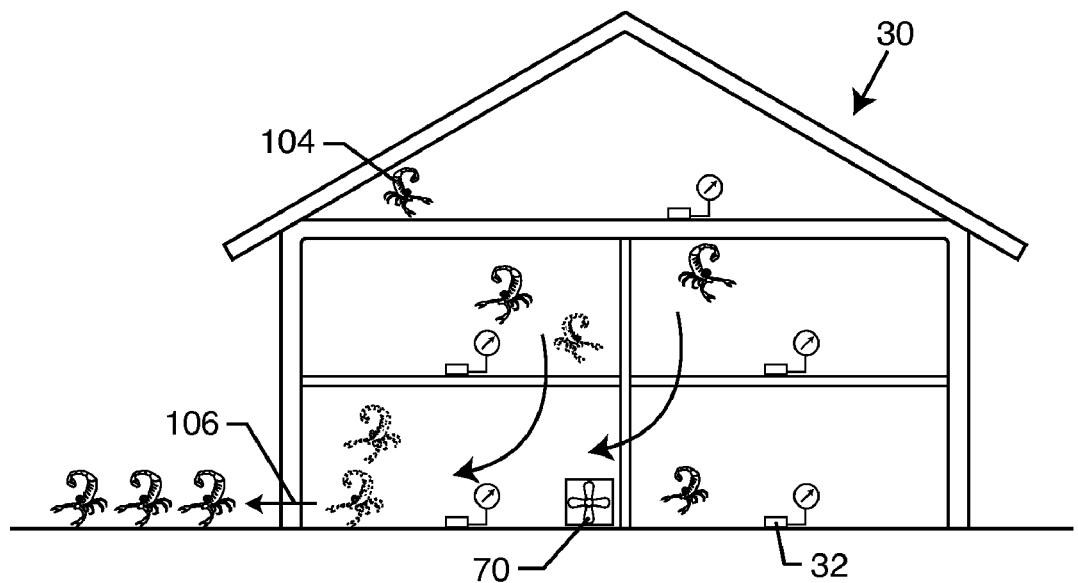
FIG. 14 is a schematic diagram showing various components of the present invention installed for treatment of a building infested with pests, such as scorpions, and the determination of an ingress/egress point in the building.
Figure 15:
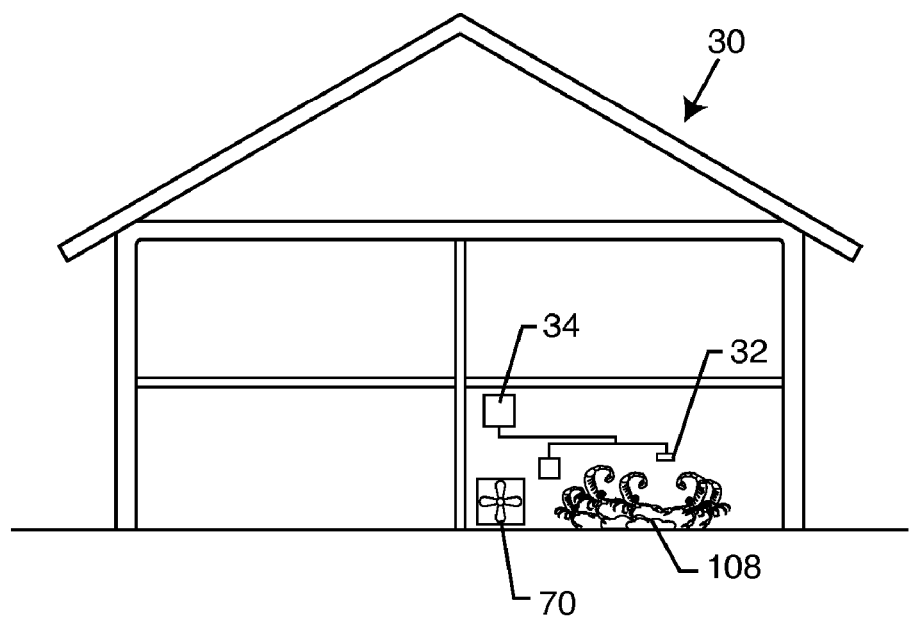
FIG. 15 is a schematic diagram showing various components of the present invention installed for treatment of pests in a single room of a building, where the pests have been drawn into that room, in accordance with the present invention.

With reference now to FIGS. 14 and 15, as described above, pests often find their way into buildings and dwellings 30. In particular, in certain southwest portions of the United States, an increasing problem is the infestation of scorpions 104 into houses and the like where the temperatures are cooler and additional moisture can be found. The incidences of scorpion stings to both humans and pets have increased as houses and buildings have been constructed in desert areas beyond the city boundaries. The present invention can be used to eradicate and remove these pests 104.

In one embodiment, as illustrated in FIG. 14, one or more heaters 70 are used to heat the entire structure 30. Temperature probes 32 are placed in selected locations within the structure 30. It will be appreciated that multiple inlet ducts may be used to import heated air, as discussed above. The air within the structure 30 is heated to a predetermined level which is lethal to the scorpions 102, or other pests. This can cause the scorpions 104 die in-situ.

Alternatively, the scorpions 104 find ingress/egress points 106 in the structure 30 and flee the structure 30. Thermal imaging devices, such as thermal imaging cameras and the like, can be used to detect the ingress/egress points 106, such as by viewing the scorpions or rodents 104 fleeing the structure 30, or more typically the heated air escaping from such points 106. These points can then be sealed by using caulking material and the like to prevent future infestation.

With reference now to FIG. 15, in another embodiment, the pests 106 can be attracted to one location within the structure 30, such as a single room, a garage, basement, etc., using an attractant 108. The attractant may comprise a bait in the case of rodents and the like, or a wet towel or rug in the case of scorpions 104 which are attracted to the moisture in a wet towel or rug. Placement of the wet towel or rug in the desired room can attract scorpions 104 overnight. The next morning, the heater 70 can heat the air within the room to kill or drive out the scorpions 104, as described above.

Figure 16:
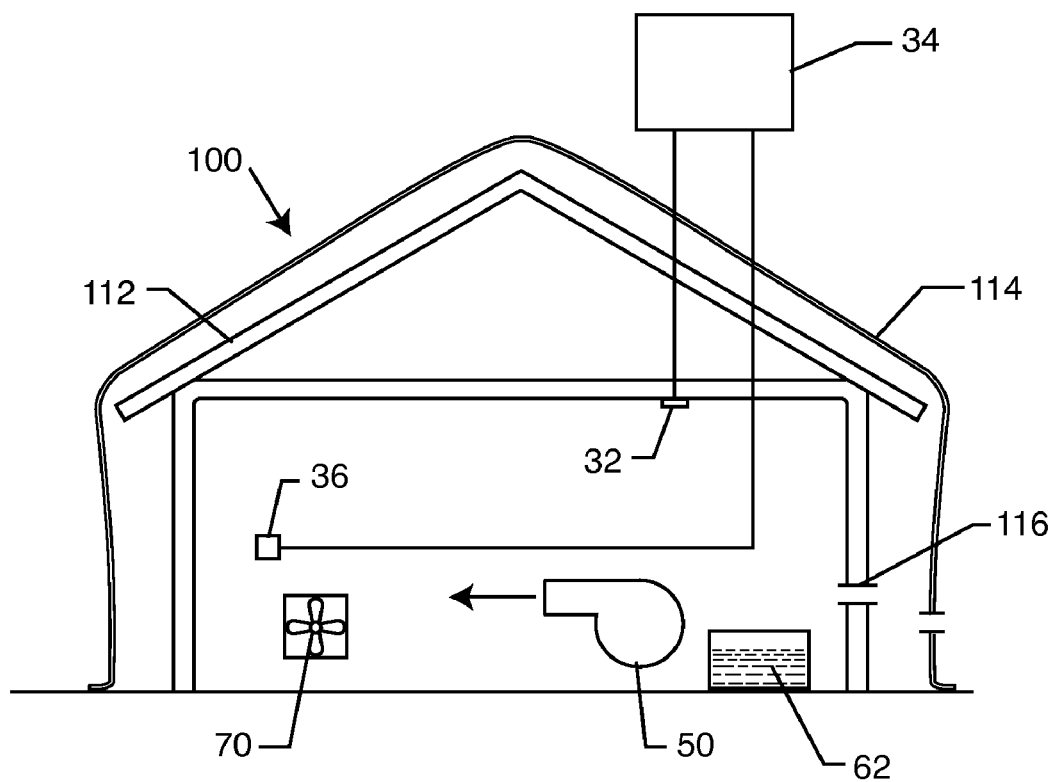
FIG. 16 is a schematic diagram showing various components of the present invention installed for removing moisture from a partially constructed building, in accordance with the present invention.

With reference now to FIG. 16, the method of the present invention can be advantageously used to dry building materials of a partially constructed or flood damaged building, such as the illustrated structure 110. Typically, the present invention is performed after the framing process when the wooden framing structures have been installed in the building, but before drywall, paint, carpeting and the like are installed. Preferably, the roof 112 of the structure has already been constructed. Additionally, preferably the outer brick, stucco, etc. is also present, but is not required. The at least partially finished roof and exterior can create a sufficient enclosure for the purposes of this embodiment. However, in other instances, such as when the exterior or roof is not completed, a tent 114, comprised of tarps or the like, is extended around the partially constructed building 110 so as to substantially enclose it.

The necessary components are installed, such as illustrated internal electric heater 70 (although other heating methods can be employed such as the previously described heat exchanger and exterior heater with inlet ducts). Probes such as temperature probes 32 and the like are preferably used and linked to a console. Blowers and fans 50 can be used to aggressively move the heated air within the partially constructed building 110 so as to evenly disburse the heated air, and create a positive pressure such that the heated air will exit the building through an opening 116, such as an open window or unfinished opening, and an opening in the tarp tent structure 114.

As discussed above, lumber that has too high a moisture content can lead to mold colonization, odors, shrinkage resulting in drywall problems, and ultimately potential health and legal issues to the builder. Lumber that is wet during the framing stages, whether it arrives wet or becomes wet at the job site, is a problem if it is not allowed the time to dry. With the requirements to build homes quickly, the moisture problem may not be adequately addressed.

In lieu of the purchase of expensive kiln-dried lumber, the present invention can be used to improve the quality of homes and buildings produced and at a lower cost, with decreased quality problems, warranty costs, and construction defect lawsuits.

The ambient air within the partially constructed building 110 is heated to above ordinary ambient temperatures, such as between 100° F. and 400° F. The air conveys the heat to the wood and carries away evaporated moisture. Lumber dries from the outside to the inside. Water is contained in wood cells in two ways. The first level of moisture in wood is found in the cell cavity as "free" water. The second level is water absorbed in the cell wall as "bound" water. Green lumber is defined as having the cell wall saturated and a variable amount of liquid or "free" water in the cell cavities. Once all the "free" water has been removed from the wood and the cell walls remain fully saturated, the lumber is at the "fiber saturation point". Stated in terms of moisture content, green lumber typically exceeds 25% to 30% moisture content. A reduction of moisture content from the fiber saturation point occurs as the "bound" water is removed from the cell walls. The wood begins to experience shrinkage and the wood strength begins to increase. The process of drying in accordance with the present invention allows the wood to reach moisture equilibrium with the surrounding atmosphere, typically less than 15% moisture content.

Over the period of only a few days, the desired moisture removal can take place using the method of the present invention. Devices such as de-humidifiers 62 or the like can be used to remove moisture from the heated air to facilitate the process. Once the proper moisture content has been achieved, the overall frame structure has increased dimensional stability as the frame will not experience significant shrinkage or swelling, and their attendant problems. Fungal attacks will generally not occur in dry wood. If the wood used for framing happens to include any insects or larvae, such as dry wood termites or beetles, these insects will most likely be destroyed. Due to the drying process, the framing is further enhanced for additional treatment, such as gluing, application of fire retardants and paints, etc. The same process can be utilized during the mudding process during drywall installation to facilitate the drying of the drywall mud such that the interior can be painted more quickly.

With reference to FIGS. 17-19, although the present invention has been described in use with association with houses and other buildings and large structures, the present invention can also be used in association with other structures, such as vehicles. FIGS. 17-19 illustrate the present invention used in association with a car 118, train 120, and airplane 122. Such vehicles can have high levels of VOCs, can become infested with insects and rodents, or can be contaminated with harmful biological microorganism and allergens and the like. Moreover, such vehicles can be damaged by water, and thus needs to be dehumidified and dried out quickly while killing any mold or fungi. Any or all of the aforementioned steps and components can be implemented in such treatment methodology for vehicles and other such structures.

Although the above description has been directed to rather large structures, such as residential or commercial buildings, and passenger occupiable vehicles, and the like, the present invention can also be applied to treatment of much smaller areas or objects. For example, a single room of a building may be treated by sealing the windows, doors, and other passageways of that particular room or area and treating such area, as described above. There are also instances where small personal articles, such as clothing or bedding, or even furniture is required to be treated, but not the structure itself.

Figure 20:
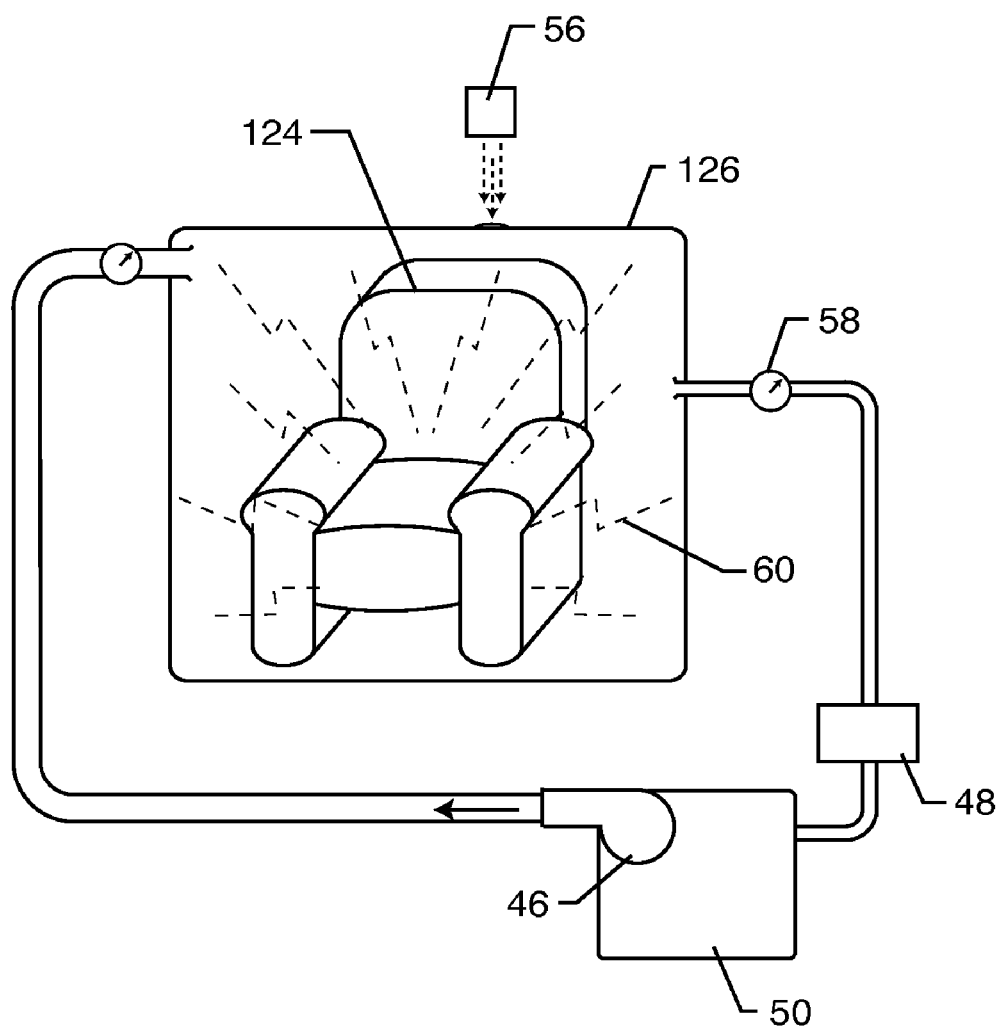
FIG. 20 is a schematic diagram illustrating an object within an enclosure to be treated in accordance with the present invention.

As illustrated in FIG. 20, the present invention can be adapted for treatment of such articles 124. A common instance of treatment is the destruction or removal of allergens such as dust mite feces and the like from bedding and mattresses. Dust mite feces are known to cause mild and even severe allergic reactions in some individuals. These individuals may have headaches, runny noses, persistent coughs, etc. which is not caused by an infection, but rather allergic reaction to the allergens. The personal articles 124, in the form of bedding or the like, is placed within a portable structure 126. Such portable structure 126 may comprise a rigid and portable structure of sufficient size to treat the articles. For example, the back of a van may be converted into a treatment containment area. Alternatively, an inflatable bag, typically comprised of appropriate thermal material, is used. The personal articles 124 are placed within such a thermal envelope or bag 126 and heated air directed into the inlet thereof. Pressure and temperature could be monitored and controlled using a device 58 or sensors attached to the portable structure 126. Preferably, the heated air which is removed is passed through a filter 48 and re-circulated, as described above. If toxic molds or fungi are of a concern, the air temperature may be reduced over time to prevent sporulation and the like.

It will be appreciated by those skilled in the art that the present invention is typically mobile so as to be transferred to this site to be treated. For example, when treating a large vehicle (such as a train or airplane), a building or the like, the necessary heaters, ducts, probes, any necessary tinting, thermal blankets, etc., are transferred to the vehicle, building, etc., to be treated. Thus, the entire structure, or even just a portion thereof, can be treated in accordance with the present invention in a very convenient manner.

Figure 21:
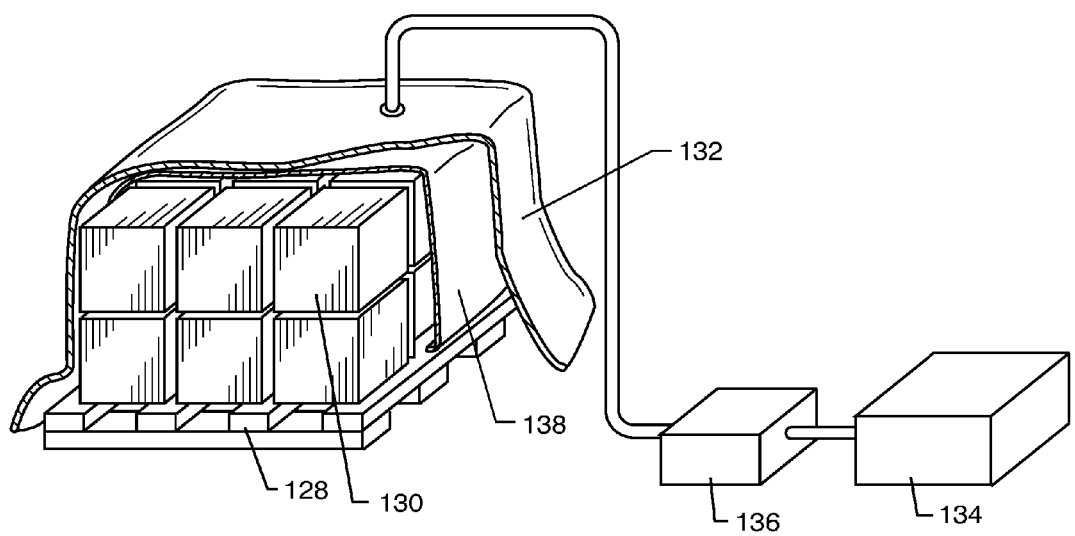
FIG. 21 is a schematic diagram illustrating treatment of contaminated pallets and cargo goods, in accordance with the present invention.

With reference now to FIG. 21, another application of the present invention is the treatment of insect infested or fungus/mold contaminated pallets 128. U.S. Pat. No. 6,612,067 to Topp discloses an apparatus for and method of eradicating pests in pallets using a heated chamber. However, the Topp Patent is limited in that only a fixed number of pallets can be treated at any given time. Moreover, Topp does not provide for the treatment of cargo 130 on infested pallets 128. Nor does Topp adequately deal with wood pallets which have become contaminated with fungus, mold and the like.

In an embodiment of the present invention, pallets 128, or even cargo 130 resting on pallets and the like in a shipyard, airport, etc., are inspected to determine if it is infested or contaminated with an undesirable insect or microorganism or the like. If so, the pallets, cargo, etc., is isolated. A thermal barrier 132 is created around the contaminated cargo/pallets. This may be done, for example, using tenting materials, such as tarps. In this manner, the flexible tenting or arrangement of tarps can be used to create an enclosure 132 around a very small amount of pallets 128 or contaminated cargo 130 or a very large number of pallets or contaminated cargo. Preferably, a sealing barrier is created, such as by taping the edges of the tarps to one another, placing sandbags on the bottom of the tarps, etc., so as to substantially seal and enclose the area to be treated. The air within the enclosure is then heated, such as with an internal space heater, or more typically with an external heater 134 which injects heated air into the enclosure 132. The air is heated between 110° F. to 400° F. to eradicate the microorganisms or pests. When microorganisms, such as fungus, contaminate the objects to be treated, preferably a negative pressure is created such that the air is passed through a filter 136 either while it is recirculating within the enclosure and/or before the air is allowed to pass into the atmosphere. Preferably, fans are used to aggressively move the air within the enclosure such that all pallets or containers and the like are treated and the heat is distributed relatively evenly. Moreover, probes, such as temperature probes and the like, may be inserted at selected locations within the enclosure, pallets, contaminated goods, etc., so as to ensure that adequate heat treatment is achieved. This may include the use of thermal imaging devices, such as internal thermal cameras which are monitored so as to ensure that there is sufficient heat in the areas to be treated. Alternatively, or in addition to, thermal imaging devices from outside the enclosure may be used to ensure that all contaminated objects are adequately heated.

In some instances, only the wood pallets or other containers may be infected, but not the goods or cargo. Also, in some cases, the cargo may be damaged by the elevated heat. In such cases, the goods 130 on the pallets 128 can be protected and shielded from the heat, such as by using thermal blankets 138 which prevent the heat from penetrating into the goods. Temperature probes may be placed within the goods to ensure that they are maintained at a sufficiently low temperature so as not to be damaged. In another embodiment, a secondary supply to cool air is pumped into the goods themselves, such as below the thermal or insulated blankets, ducts, and the like, so that the pallets, containers and exposed goods are treated while the protected goods are maintained at the desired temperature. Potentially, fumigant may be added to the pallets and/or cargo. By preheating the enclosure, the amount of fumigant to be used can be significantly reduced, as described above as the heat has a synergistic effect on the fumigant, pesticide, etc.

In yet another embodiment, the present invention can be used to treat non-processed food. For example, nut growers often experience the problem of insect infestation, such as meal worms and the like. This is particularly a problem in the pistachio industry where meal worms can infect the nuts, such as by boring a hole through the shell to feed on the nut inside.

Roasting the nuts at elevated temperatures for prolonged periods of time effectively kills such meal worms and other insects. However, many nuts are not roasted as this imparts a different taste and quality to the nut. Applying insecticides and other chemicals to the nuts preserves their non-roasted characteristics, but presents obvious health concerns.

Accordingly, the present invention is used to heat the nuts to a temperature sufficient to kill the meal worms or other insects which have infected the nuts, but at a temperature which is much lower than roasting temperatures, or for a period of time much less than roasting temperatures so that the nuts will have the non-roasted characteristics, flavor, etc. This can be done, for example, by passing the nuts on a conveyor system into an enclosure where the nuts are rapidly heated, and then subsequently cooled. Alternatively, the nuts can be placed in a heating room where they are heated at a relatively low temperature for a prolonged period of time, or an elevated temperature for a very short time followed by cooling. Whereas roasting temperatures are often in excess of 200° F., the temperature for killing these pests can be much lower, such as 120°-150°.

Figure 22:
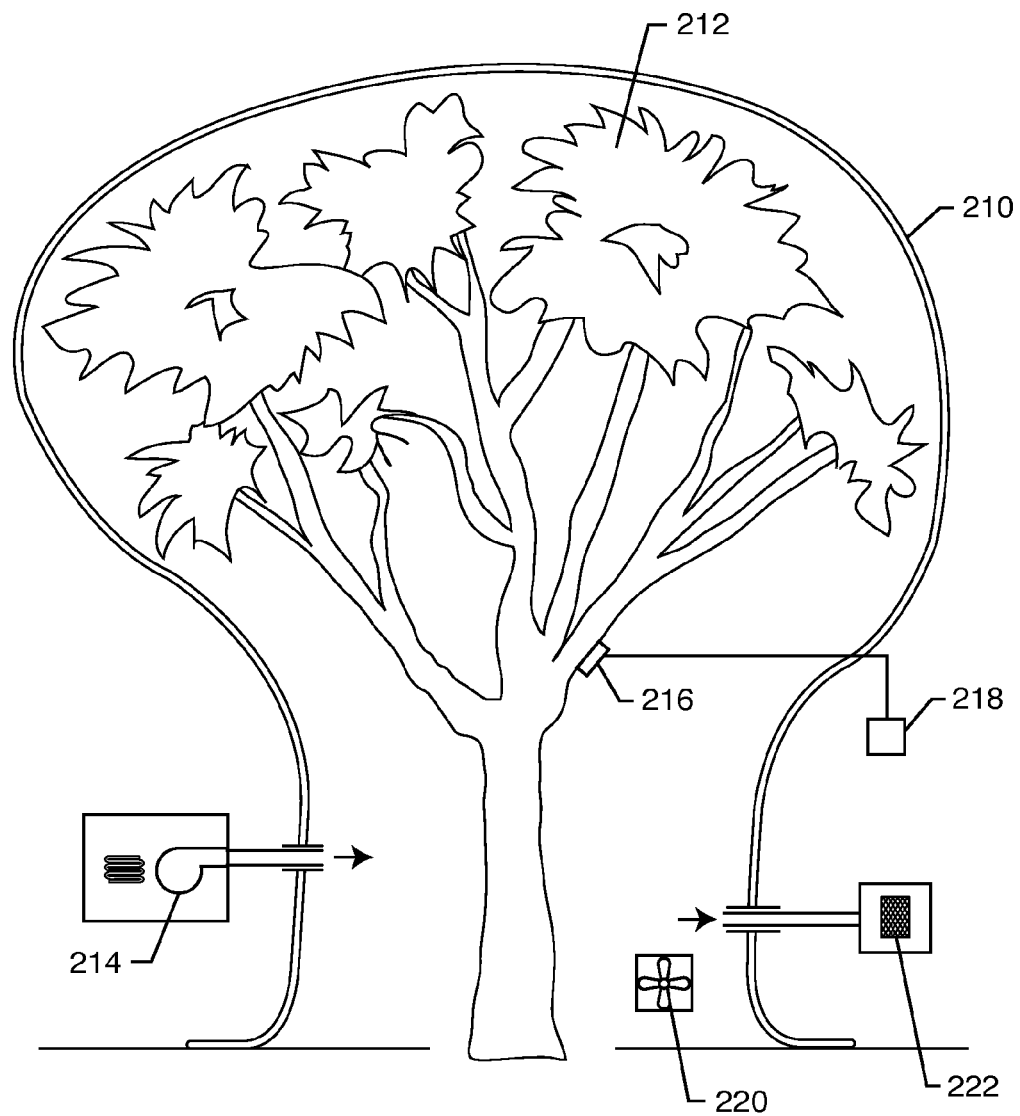
FIG. 22 is a diagrammatic representation showing a tree treated in accordance with the method of the present invention.

With reference now to FIG. 22, the present invention is also contemplated as being used for treating live plants, such as trees, which have been infected with a disease-causing microorganism or insects or the like. One such example is "Sudden Oak Death" syndrome, which is believed to be caused by a mold or fungus which infects the tree. In such case, a tarp 210 is placed over the tree 212 so as to substantially enclose it, or the plant or tree 212 is otherwise substantially enclosed. The air within the enclosure 210 is heated, such as by the illustrated heater and blower 214, although it will be understood that any of the aforementioned methods of heating the internal space within the tarp or enclosure 210 can be used, such as placing the heater inside of the enclosure 210, utilizing a conductive heating system, such as a hydronic system, the use of a solar-powered system, etc. The air within the tented enclosure 210 is raised to a temperature between 110° F. and 400° F. which is lethal to the microorganism or insect, but not lethal to the tree or plant 212. Preferably, temperature sensors 216 are used to monitor the temperature. The temperature sensors may be placed directly into the tree, the adjoining soil, positioned so as to monitor the ambient air temperature, or the temperature readings may be taken from outside of the enclosure 210. Preferably, these temperature readings are monitored, such as by console 218. In a particularly preferred embodiment, one or more fans 220 aggressively and actively circulate the heated air within the enclosure 210 such that the heat is transferred by conduction to the entire tree 212. In a particularly preferred embodiment, the air is passed through a filter 222. This may be done as the air is vented to the atmosphere, or may be done within the enclosure 210 so as to capture any contaminants, allergens, spores, and the like. In some instances, it will be appreciated that such a filter is not required as the byproducts of the process do not present a threat or danger to the remaining uninfected portion of the tree, the environment, etc.

Finally, the present invention can be utilized by municipalities and others interested in starting intentional burns of wild vegetation. In this regard, and by way of background, it is well known that throughout the American West, years of high rainfall are often followed by several years of near drought conditions. The high rainfall stimulates the growth of vegetation on, for example, hillsides and open areas adjacent to developed properties. As the vegetation dries during the summer, an extreme fire hazard develops. Municipalities have learned that it is often advantageous to conduct controlled burns of such wild vegetation to minimize fire risk to structures.

Ideally, such intentional burns are conducted on cool, high-humidity days where the fire can be properly managed. However, it has been found that it is very difficult to start the controlled burn under such conditions. As a result, the controlled burns are often started under less than ideal circumstances, resulting in the fire outrunning its handlers and burning far more than the original design. The present invention can be utilized to heat and dry some vegetation to create an artificial combustible state, which is different from its natural state, allowing the intentional burn to be started under ideal ambient conditions which allow the fire handlers to maintain better control of the intentional burn. For example, the brush area to be heated and artificially dried may be dusted with a metallic dusting material and heated with radio waves to create the desired combustible state.

Although several embodiments have been described in detail for purposes of illustration, various modifications may be made to each without departing from the scope and spirit of the invention. Accordingly, the invention is not to be limited, except as by the appended claims.

What is claimed is:

1. A method for treating a human occupiable vehicle or building structure at least partially contaminated with harmful microorganisms or insects or having objects therein contaminated with microorganisms or insects, comprising the steps of:

substantially enclosing at least a portion of the structure to be treated;

heating ambient air within the structure to a predetermined temperature of between 110° F. to 400° F. to cause the harmful microorganisms or insects in the structure to be destroyed or migrate into the ambient air;

monitoring the temperature in the structure;

injecting a metal-based material into an area of the structure, and subsequently bombarding the area with electromagnetic waves; and passing the heated air from the structure through a filter.

2. The method of claim 1, including the step of recirculating the filtered and heated air into the portion of the structure being treated.

3. The method of claim 1, wherein the heating step comprises the step of providing a heater within the structure that emits electromagnetic waves.

4. The method of claim 3, wherein the heater comprises an infrared heater to heat surfaces within the structure.

5. The method of claim 4, including the step of positioning fans adjacent to the heated surfaces within the structure.

6. The method of claim 1, including the step of positioning a plurality of fans to create a cyclone of wind within the structure.

7. The method of claim 6, including the step of positioning the fans adjacent to a heater disposed within the structure.

8. The method of claim 1, wherein the passing step includes the step of passing the heated air from the structure through an air scrubber.

9. The method of claim 1, including the step of dehumidifying the air within the structure.

10. The method of claim 1, wherein the heating step includes the step of using a hydronic heating system to heat the air within the structure.

11. The method of claim 1, wherein the heating step includes the step of burning non-fossil fuels to heat the air within the structure.

12. The method of claim 1, including the step of monitoring the moisture content of the air within the structure.

13. The method of claim 1, including the step of monitoring the level of air borne contaminants within the structure.

14. The method of claim 1, including the step of introducing heated air into a space within a wall.

15. The method of claim 14, including the step of forming an air inlet in the wall.

16. The method of claim 15, including the step of forming an air outlet in the wall.

17. The method of claim 14, including the step of removing air from the space within the wall.

18. The method of claim 17, including the step of passing the air from the space within the wall through a filter or air scrubber.

19. The method of claim 1, including the step of using a first type of heater to heat the structure during an initial heating phase, and a second type of heater to heat the structure during a later heating phase.

20. The method of claim 1, including the step of bombarding the area with radio waves having a frequency that heats the metal-based material.

21. The method of claim 1, including the step of physically cleaning a contaminated portion of the structure prior to the heating step.

22. The method of claim 1, including the step of physically cleaning a contaminated portion within the structure after determining that adequate treatment has occurred.

23. The method of claim 1, wherein the filter comprises a high or ultra-high efficiency particulate arrestance filter.

24. The method of claim 1, including the step of protecting heat-sensitive articles within the structure.

25. The method of claim 1, including the step of establishing a pressure within the structure and monitoring the pressure within the structure.

26. The method of claim 25, including the step of positioning a manometer within the structure to measure the pressure within the structure.

27. The method of claim 1, including the step of aggressively moving air within the structure to aerosolize biological and organic substances to facilitate their removal.

28. The method of claim 1, wherein the monitoring step includes the step of positioning a plurality of temperature probes at predetermined locations relative to the structure.

29. The method of claim 1, wherein the structure comprises at least a portion of a building or a vehicle.

30. The method of claim 1, including the step introducing a biocide, fungicide, or pesticide into the structure.

31. The method of claim 1, including the step of irradiating contents within the structure with ultra-violet light.

32. The method of claim 1, including the step of establishing the level of VOCs, MVOCs or pests, in the structure utilizing a gas chromatograph or an electronic nose.

33. A method for treating a human occupiable vehicle or building structure at least partially contaminated with harmful microorganisms or insects or having objects therein contaminated with microorganisms or insects, comprising the steps of:

injecting a metal-based material into an area of the structure; and subsequently bombarding the area with electromagnetic waves.

34. The method of claim 33, including the steps of heating ambient air within the structure to a predetermined temperature of between 110° F. to 400° F., and passing the heated air from the structure through a filter.

35. The method of claim 33, including the step of bombarding the area with radio waves having a frequency that heats the metal-based material.

36. The method of claim 33, including the step of irradiating contents within the structure with ultra-violet light.

37. The method of claim 33, including the step of establishing the level of VOCs, MVOCs or pests, in the structure utilizing a gas chromatograph or an electronic nose.

38. The method of claim 33, including the step introducing a biocide, fungicide, or pesticide into the structure.

39. The method of claim 34, wherein the filter comprises a high or ultra-high efficiency particulate arrestance filter.

40. The method of claim 34, wherein the passing step includes the step of passing the heated air from the structure through an air scrubber.

41. The method of claim 33, including the step of dehumidifying the air within the structure.

* * * * *